(12) United States Patent
Sayers et al.

(10) Patent No.: US 8,011,133 B2
(45) Date of Patent: Sep. 6, 2011

(54) METHOD AND APPARATUS OF HIGH-THROUGHPUT POLLEN EXTRACTION, COUNTING, AND USE OF COUNTED POLLEN FOR CHARACTERIZING A PLANT

(75) Inventors: Adda Sayers, Urbandale, IA (US); Dean M. Tranel, Madrid, IA (US); Travis A. Hanselman, Johnston, IA (US); Stephen D. Strachan, Oxford, PA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 688 days.

(21) Appl. No.: 11/823,140

(22) Filed: Jun. 27, 2007

(65) Prior Publication Data

US 2009/0000188 A1     Jan. 1, 2009

(51) Int. Cl.
*A01B 79/00*     (2006.01)
*A01B 79/02*     (2006.01)
*A01C 1/00*      (2006.01)
*A01G 1/00*      (2006.01)
*A01H 3/00*      (2006.01)

(52) U.S. Cl. .................................... 47/58.1 R
(58) Field of Classification Search .................. 800/294, 800/295; 435/420; 47/58.1 R, 58.1 SE
See application file for complete search history.

(56) References Cited

U.S. PATENT DOCUMENTS
2006/0225155 A1*  10/2006  Kumlehn ..................... 800/294

OTHER PUBLICATIONS

Aylor, D.E., "Quantifying maize pollen movement in a maize canopy", 2005, Agric. For. Meteorol. 131:247-256.
Baltazar, B.M. et al., "Pollination between maize and teosinte: An important determinant of gene flow in Mexico", 2005, Theor. Appl. Genet. 110:519-526.
Bassetti, P. et al., "Floral asynchrony and kernel set in maize quantified by image analysis", 1994, Agron. J. 86:699-703.
Dukhovnyi, A.E., "The electric charge of maize pollen as a quantitative character" (in Russian). 1975, Kolichestven. priznaki mutantov kukuruzy Kishinev: Stiinca., p. 21-24.
Flottum, P.K. et al., "A quantitative sampling method for airborne sweet corn pollen under field conditions" 1984, Crop Sci. 24:375-377.
Fonseca, A.E. et al., "Simulating potential kernel production in maize hybrid seed fields", 2004, Crop Sci. 44:1696-1709.
Fonseca, A.E. et al., "Application of fluorescence microscopy and image analysis for quantifying dynamics of maize pollen shed", 2002, Crop Sci. 42:2201-2206.
Fonseca, A.E., et al., "Tassel morphology as an indicator of potential pollen production in maize [Online]", 2003 Available at: www.plantmanagementnetwork.org/pub/cm/research/2003/tassle,   15 pages.
Goss, J.A., "Development, physiology, and biochemistry of corn and wheat pollen", 1968, Bot. Rev. 34:333-358.

(Continued)

*Primary Examiner* — Kent L Bell
(74) *Attorney, Agent, or Firm* — Alston & Bird LLP

(57) ABSTRACT

An apparatus and method of quantitatively obtaining a measurement of pollen of a plant. One method of counting comprises imaging the sample with the pollen well-distributed in the focal plane of the imager. Image evaluation software can identify and count objects in the image that are consistent with pollen. Total pollen count for the plant can be derived from the count of pollen of the sample, proportionality of the sample volume to the starting volume, and proportionality of area of sample imaged to total area of sample. Pollen quantification can be used for research or commercial production decisions relative to the plant or its seed.

12 Claims, 29 Drawing Sheets

OTHER PUBLICATIONS

Hall, A.J. et al., "The effect of water stress and genotype on the dynamics of pollen-shedding and silking in maize", 1982, Field Crops Res. 5:349-363.

Hsu, S.Y. et al., "Relative stage duration of microsporogenesis in maize", 1981, Iowa State J. Res. 55:351-373.

Hsu, S.Y. et al., "Development pattern of microspores in Zea mays L. The maturation of upper and lower florets of spikelets among an assortment of genotypes." 1988, Maydica 33:77-98.

Kiesselbach, T.A., "The structure and reproduction of corn", 1949, Agric. Exp. Stn., Res. Bull. No. 161. Univ. of Nebr. College of Agriculture, Lincoln, NE., pp. 36-49.

Kumar, D. et al., "Correlation between pollen diameter and rate of pollen tube growth in maize (Zea mays L.)", 1980, Indian J. Exp. Bot. 18:1242-1244.

Sadras, V.O. et al., "Kernel set of the uppermost ear in maize: I. Quantification of same aspects of floral biology", 1985, Maydica 30:37-47.

Uribelarrea, M. et al., "Pollen production, pollination dynamics, and kernel set in maize", 2002, Crop Sci. 42:1910-1918.

Bedinger et al., Developmental staging of maize microspores reveals a transition in developing microspore proteins, 1990, Plant Physiol. 92, pp. 474-479.

Elvanol as a binder/film former, 2005 [online], [retrieved on Sep. 15, 2009]. Retrieved from the Internet <file://C:\documents and Settings\FOGGLC.DUPONTNET\Desktop\ip_newsite\indpoly_oldsite\elv...> one page.

Fox et al. Rapid Image Analysis for counting engorged pollen grains of rice. 2001 [oneline], [retrieved on Aug. 17, 2009]. Retrieved from the Internet <http://www.regional.org.au/au/asa/2001/p/5/fox.htm> 5 pages.

Kannely, Preparation and quantification of entomophilous pollen using sonication and an area-counting technique. Madrono, vol. 52, No. 4, pp. 267-269, 2005.

Li et al. Impact of pollen grains form Bt transgenic corn on the growth and development of Chinese tussah silkworm, *Antheraea pernyi* (Lepidoptera: Saturniidae) Environ. Entomol. 34(4): 922-928 (2005).

Waring Heavy Duty Blender 2001 [online], [retrieved on Sep. 15, 2009]. Retrieved from the Internet <http://web.archieve.org/web/20011120175701/http://productsforhealth.com/waringblender.h...> 3 pages.

Qiu et al. A simple and effective method for isolating RNA from Alfalfa pollen. Plant Molecular Biology Reporter 12(3) 1994, pp. 209-214.

Mande et al. Fermentation of Bassia Flowers, Industrial and Engineering Chemistry, vol. 41, No. 7, pp. 1451-1454, 1949 [online] [retrieved on Sep. 17, 2009]. Retrieved from the Internet at <http://pubs.acs.org>.

Tranel, D. M., *Morphology and plasticity of maize (Zea mays L.) male inflorescence development and pollen production*, Dissertation, Iowa State University, DAI-B68/07 (Jan. 2008), pp. 1-100.

* cited by examiner

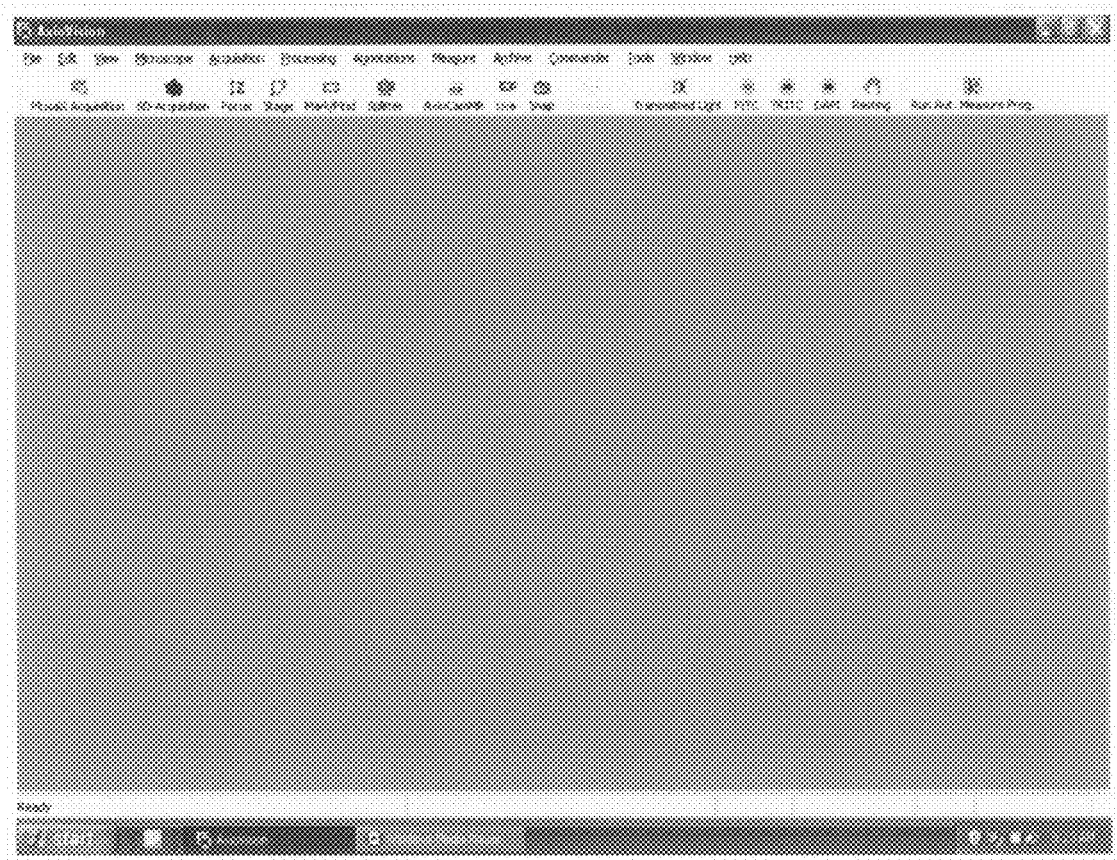
Fig.10.1

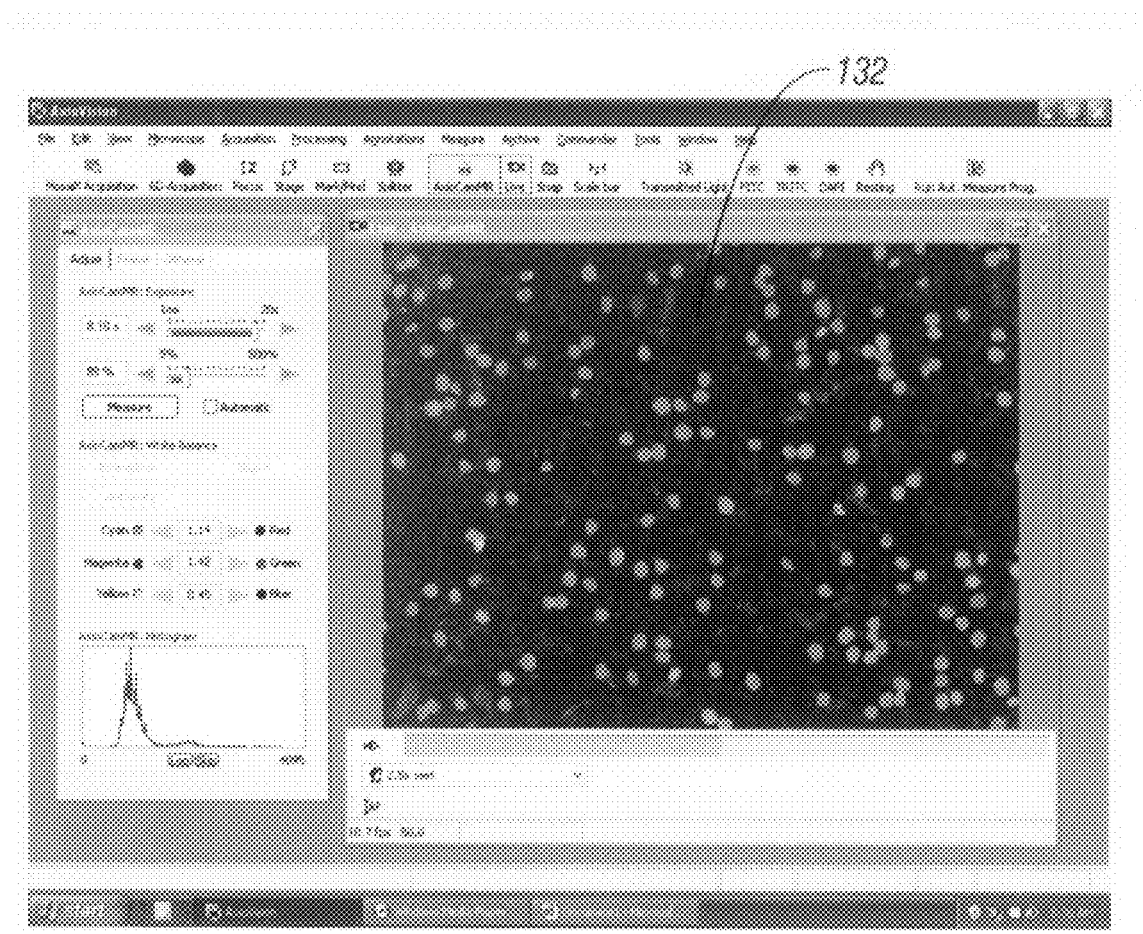
Fig. 10.2

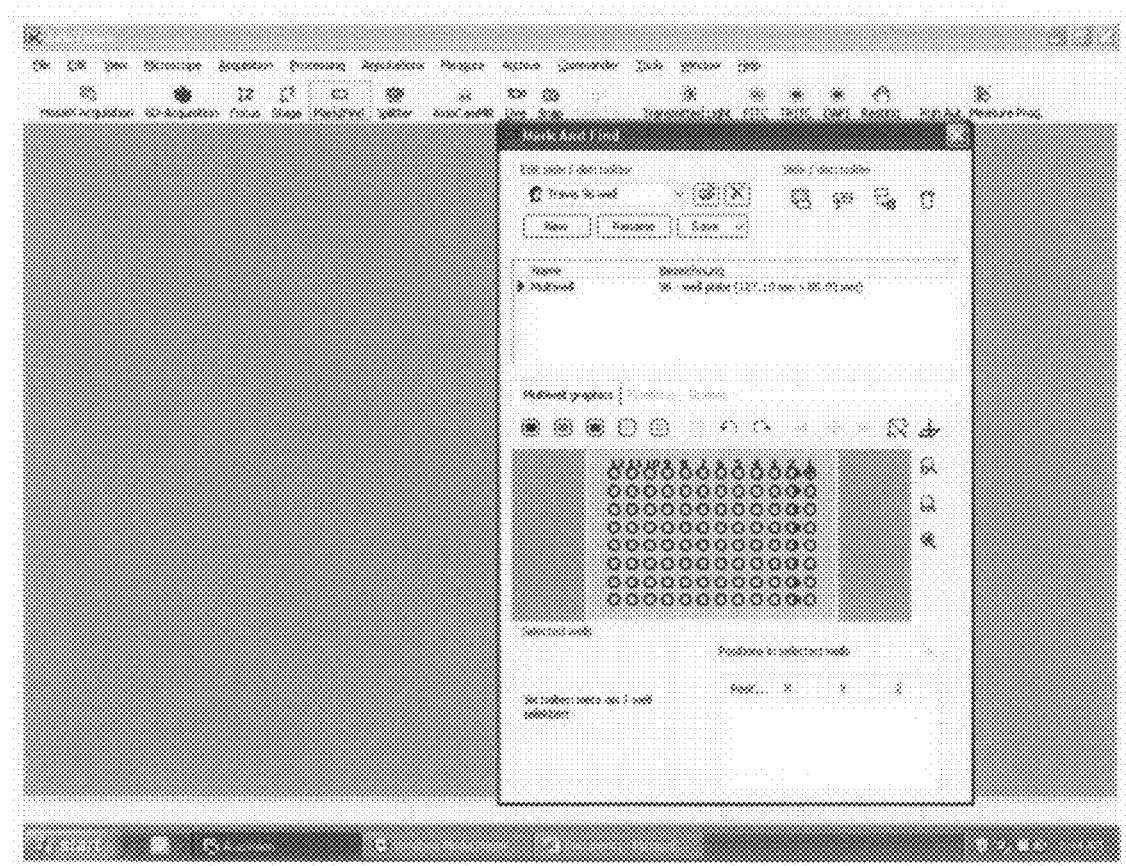
Fig. 10.3

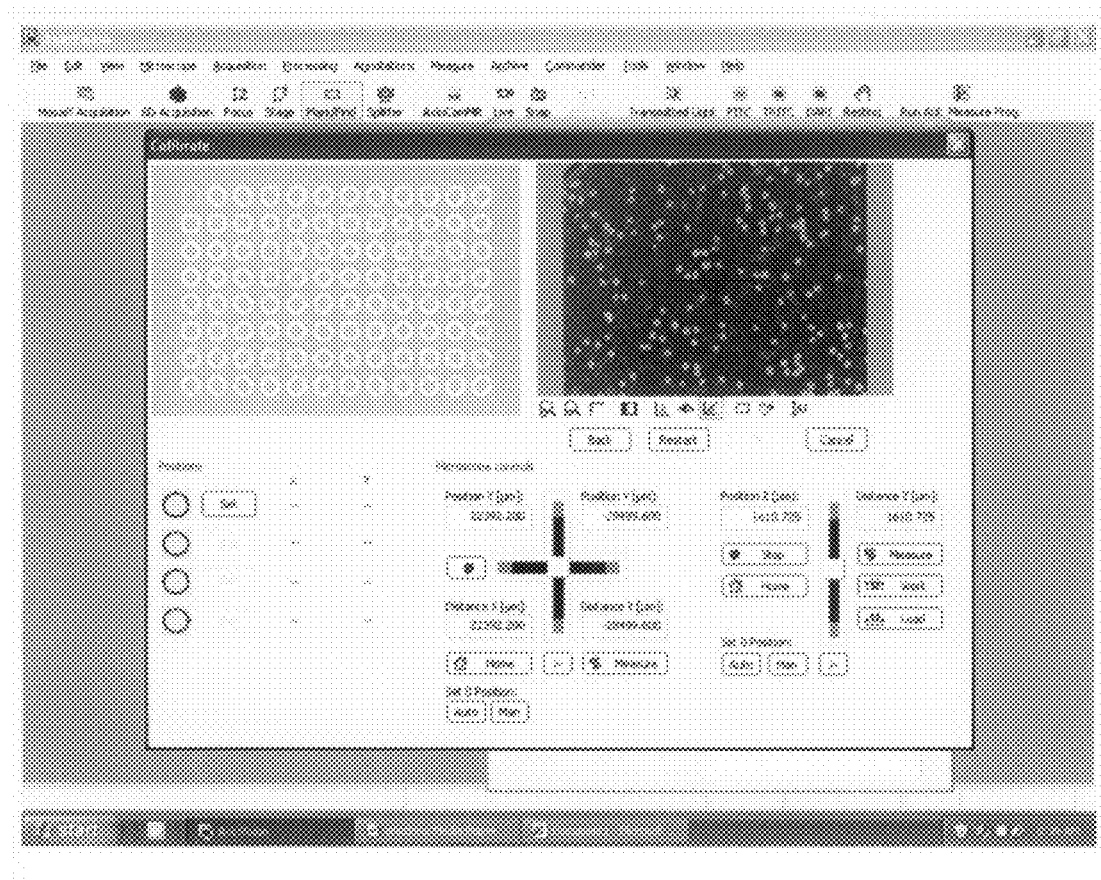
Fig. 10.4

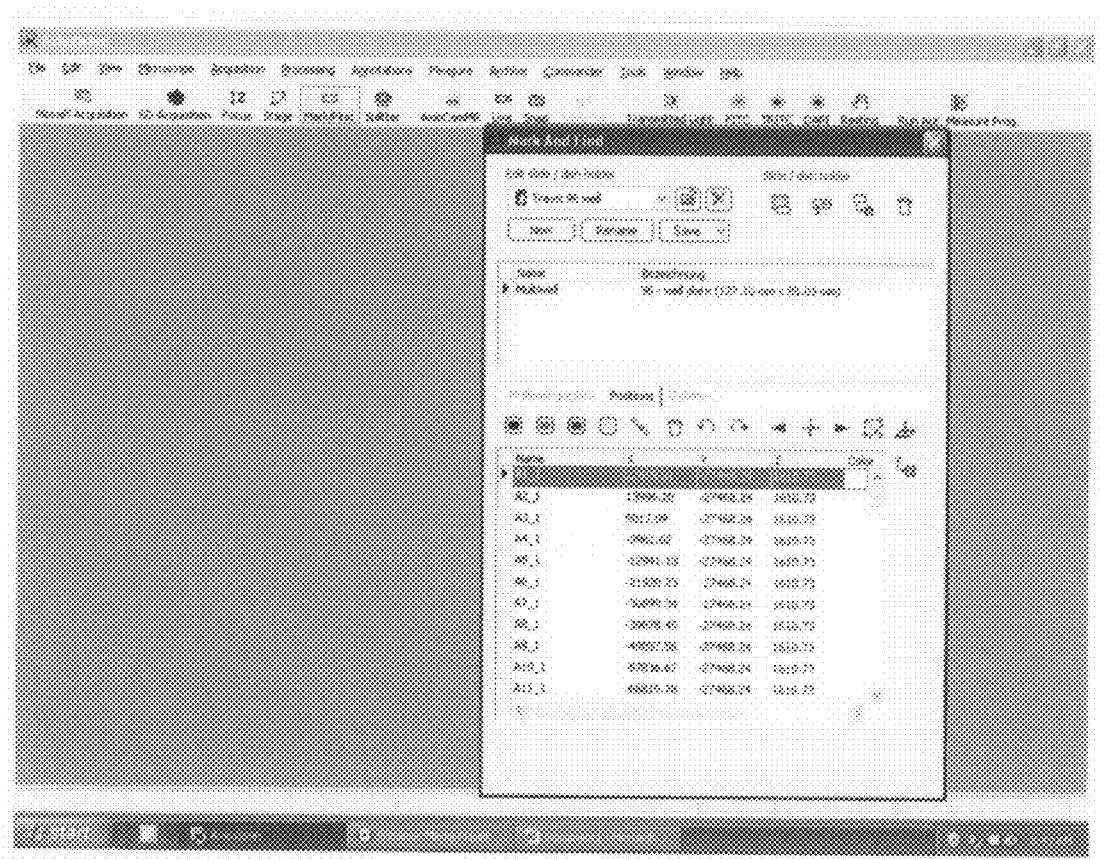
Fig.10.5

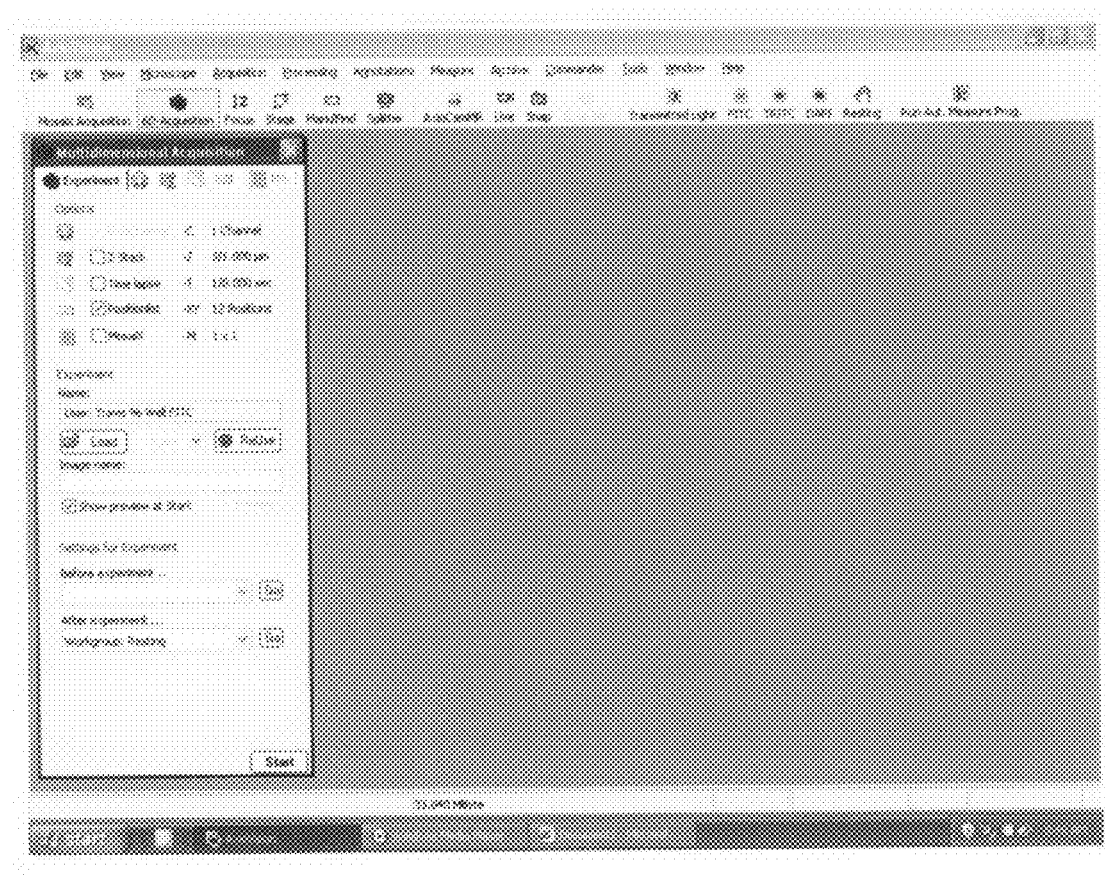
Fig. 10.6

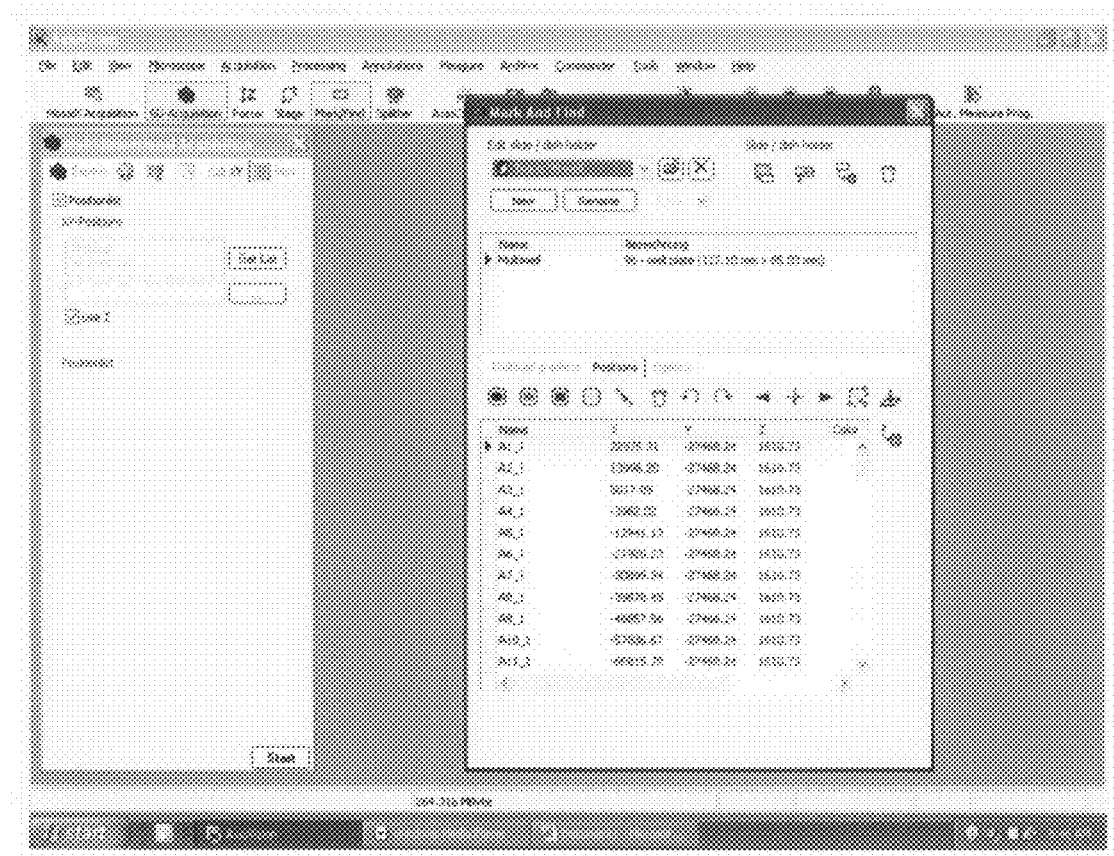
Fig.10.7

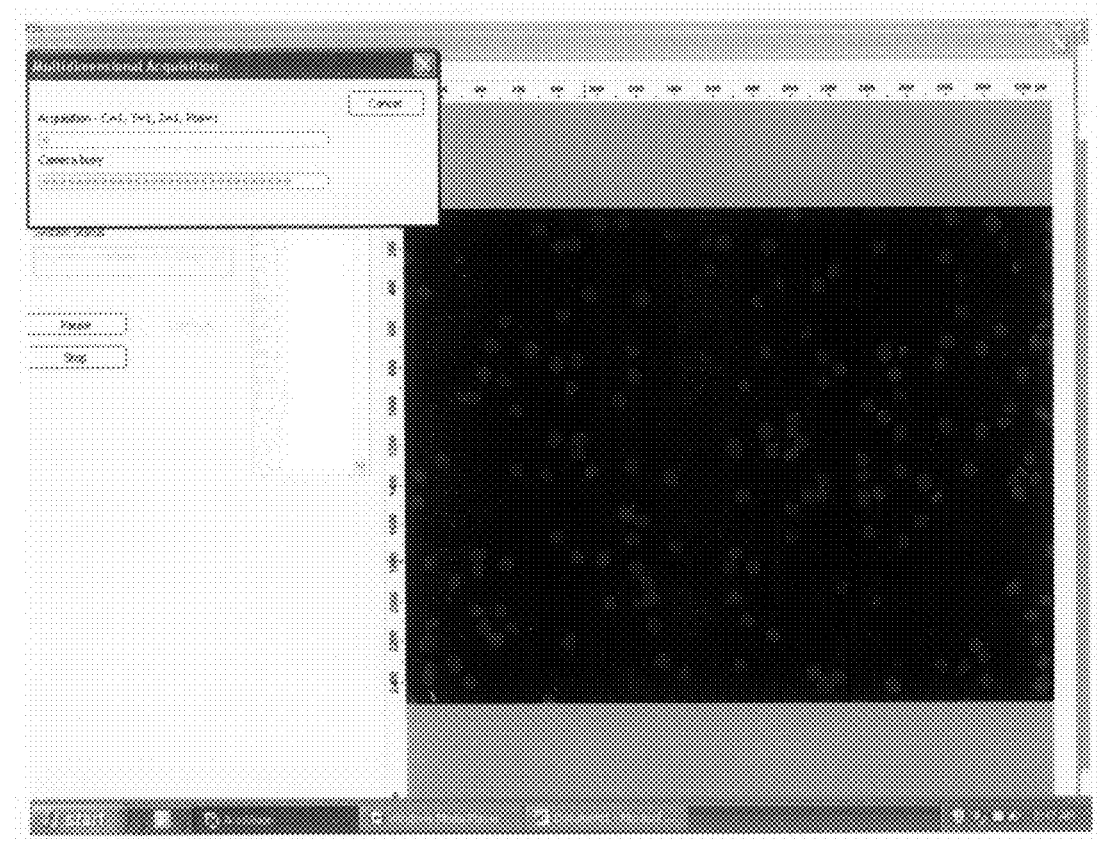
Fig. 10.8

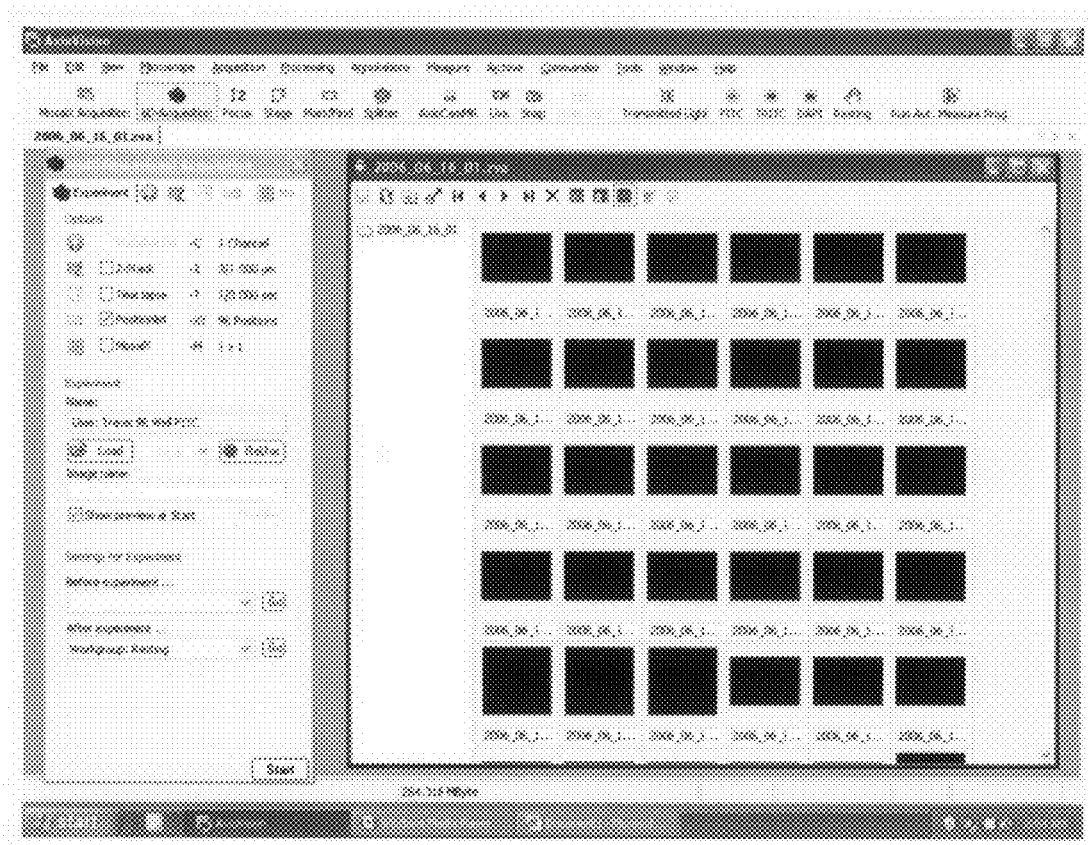
Fig. 10.9

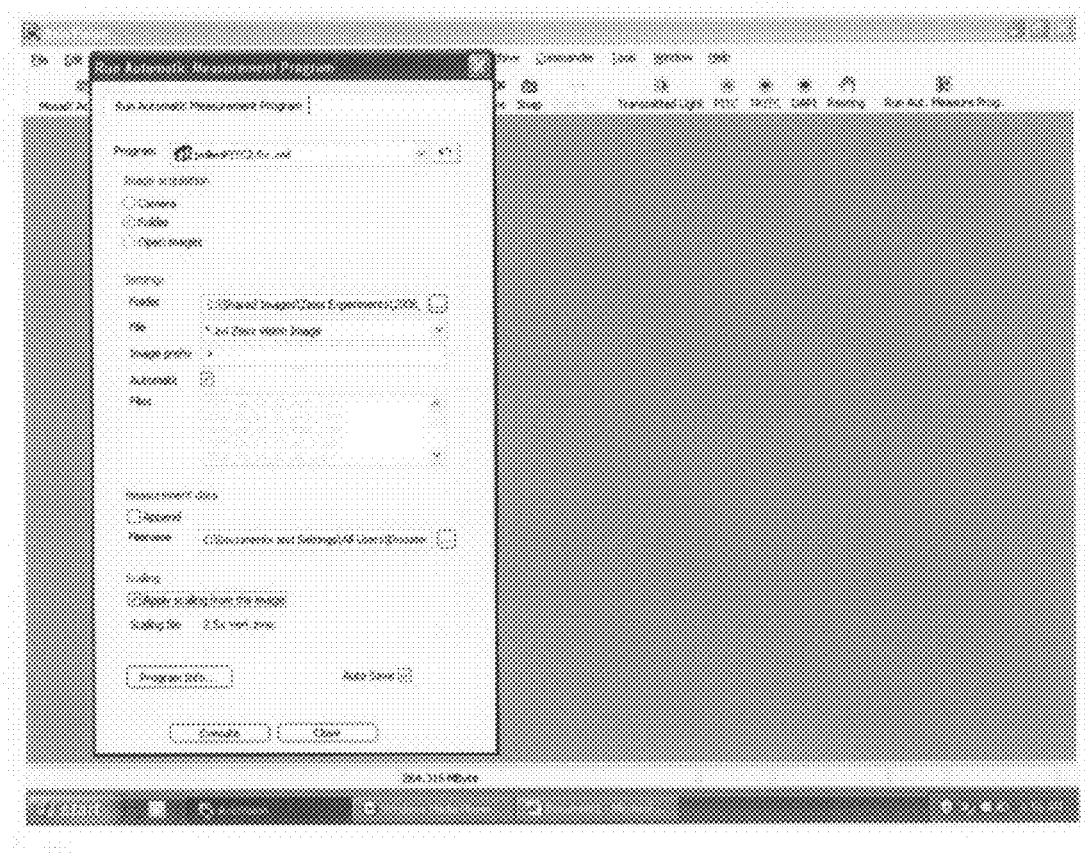
Fig.10.10

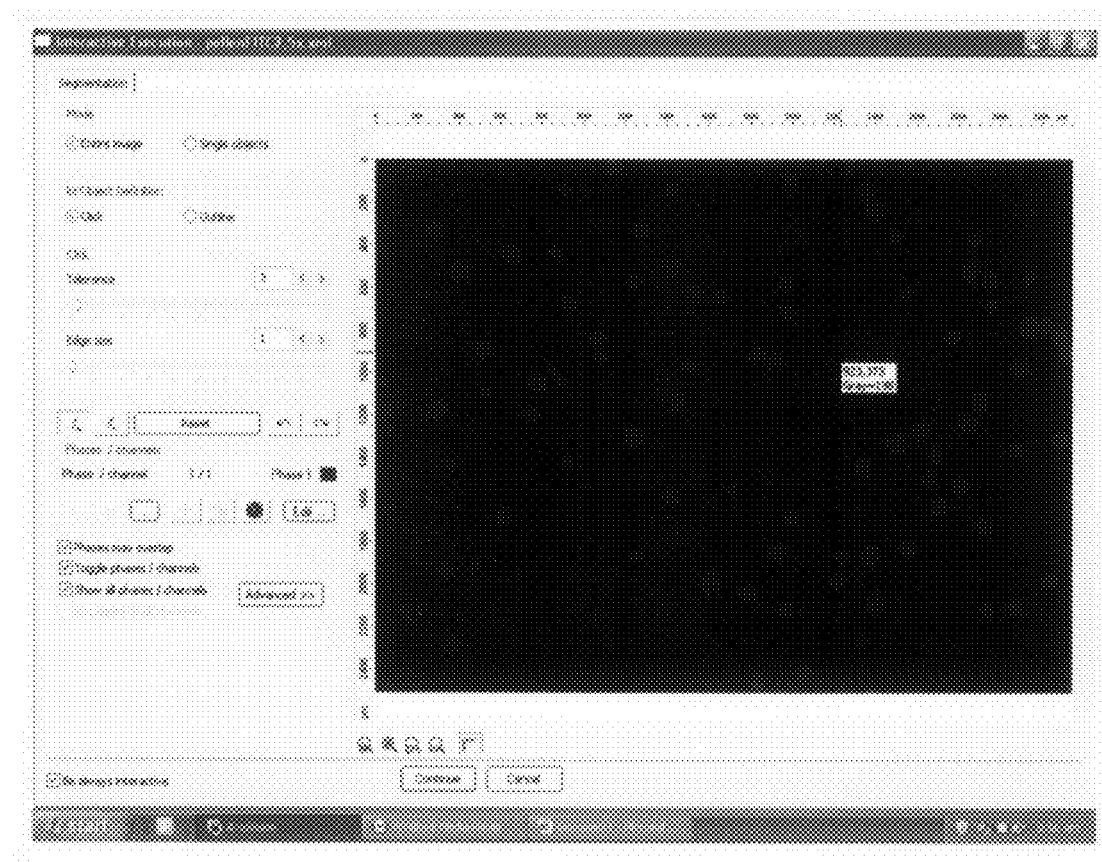
Fig.10.11

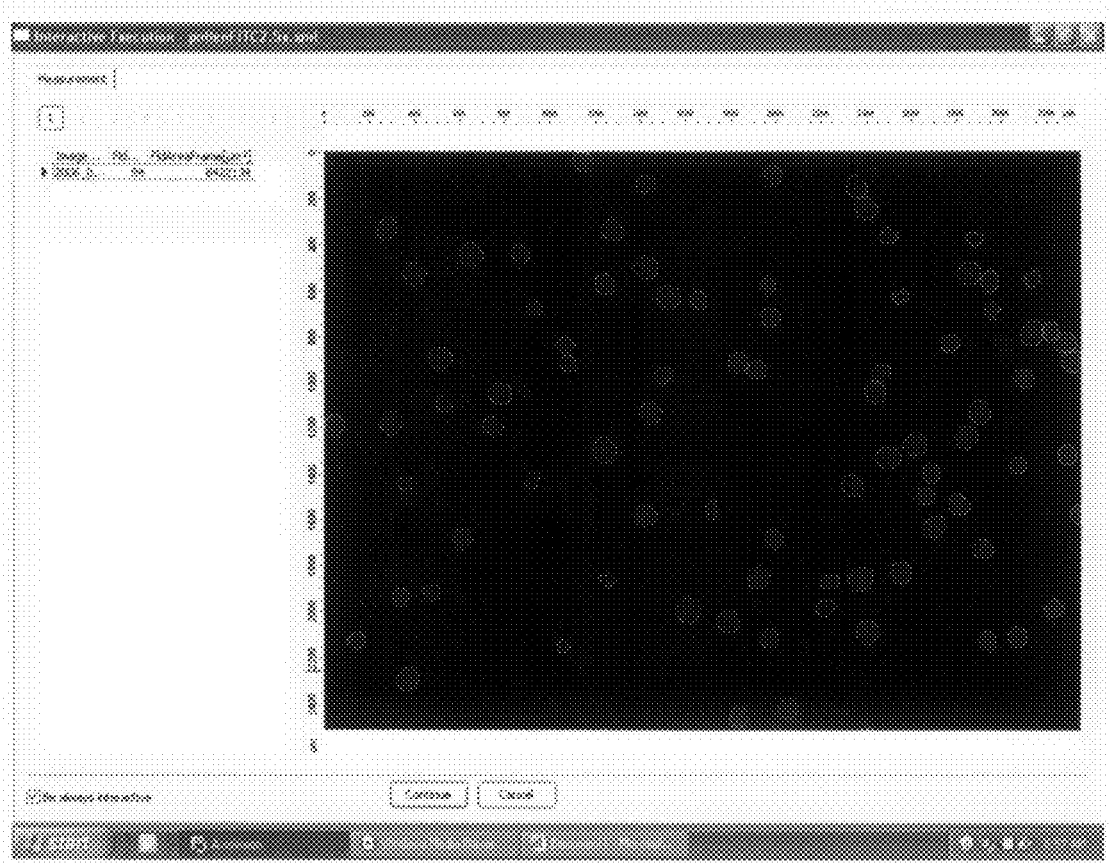
Fig.10.12

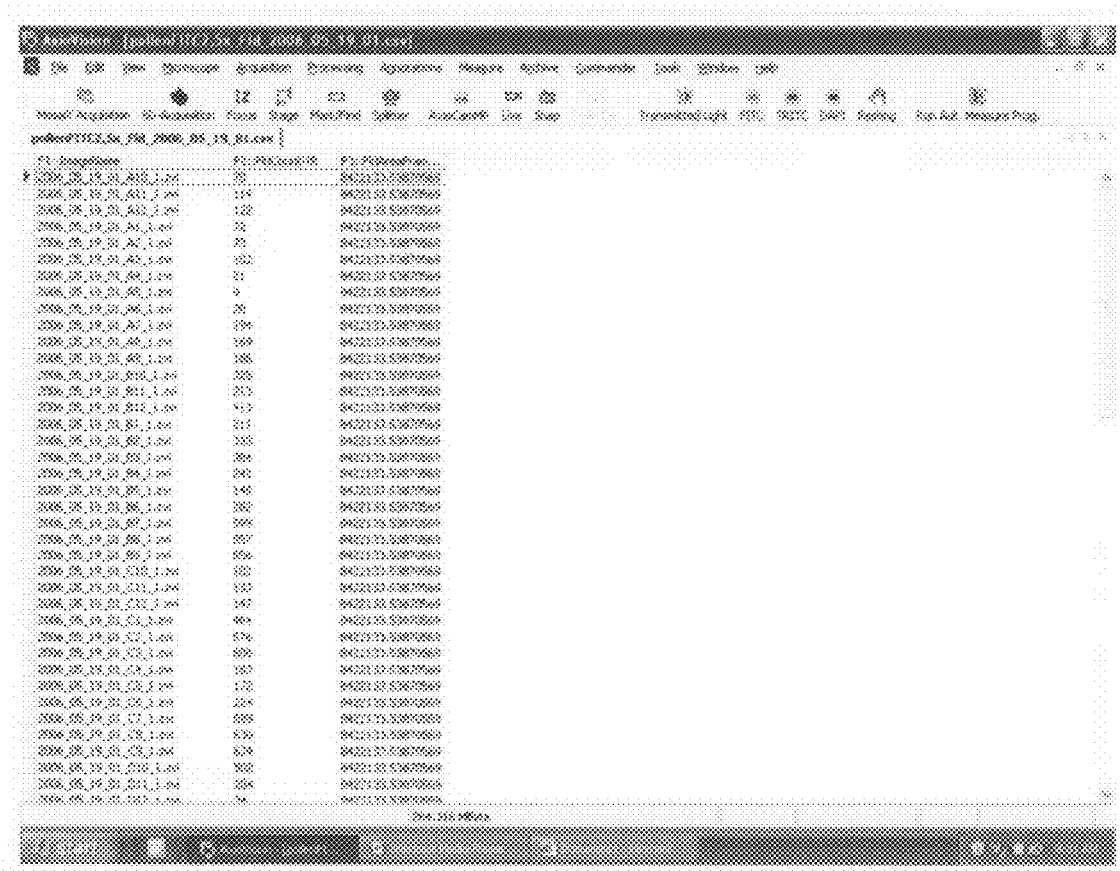
Fig.10.13

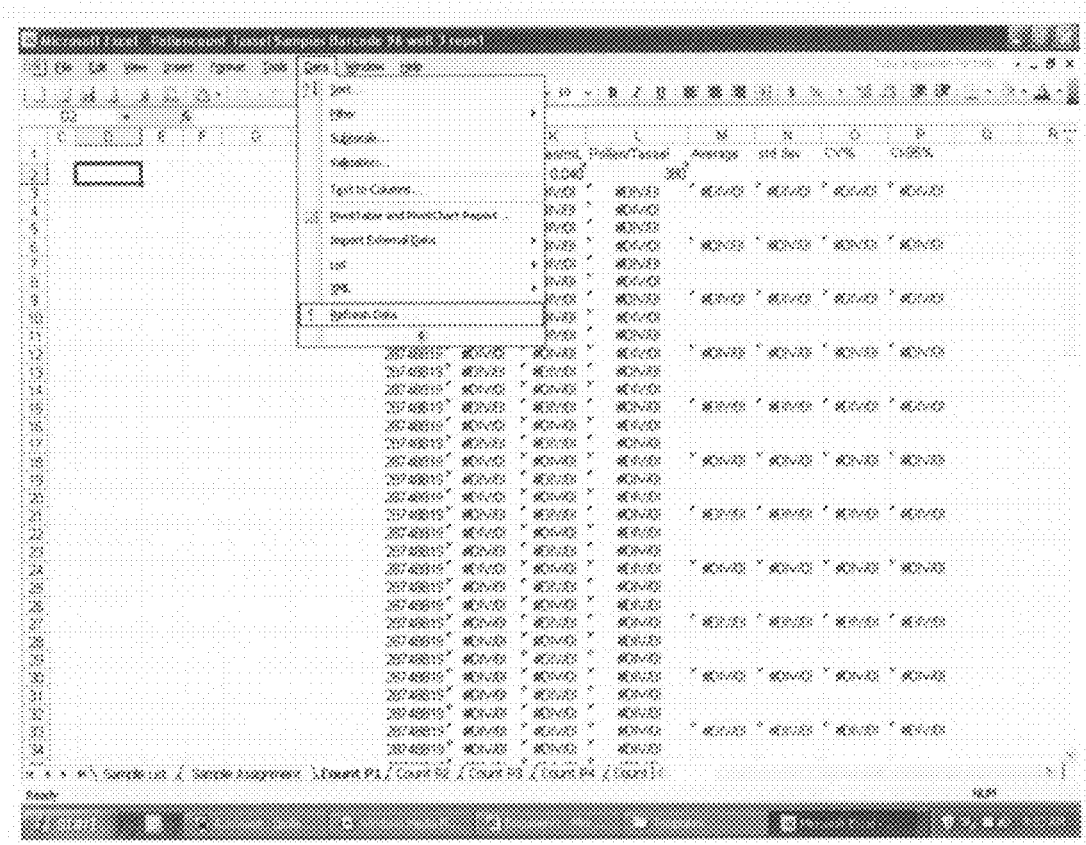
Fig. 10.14

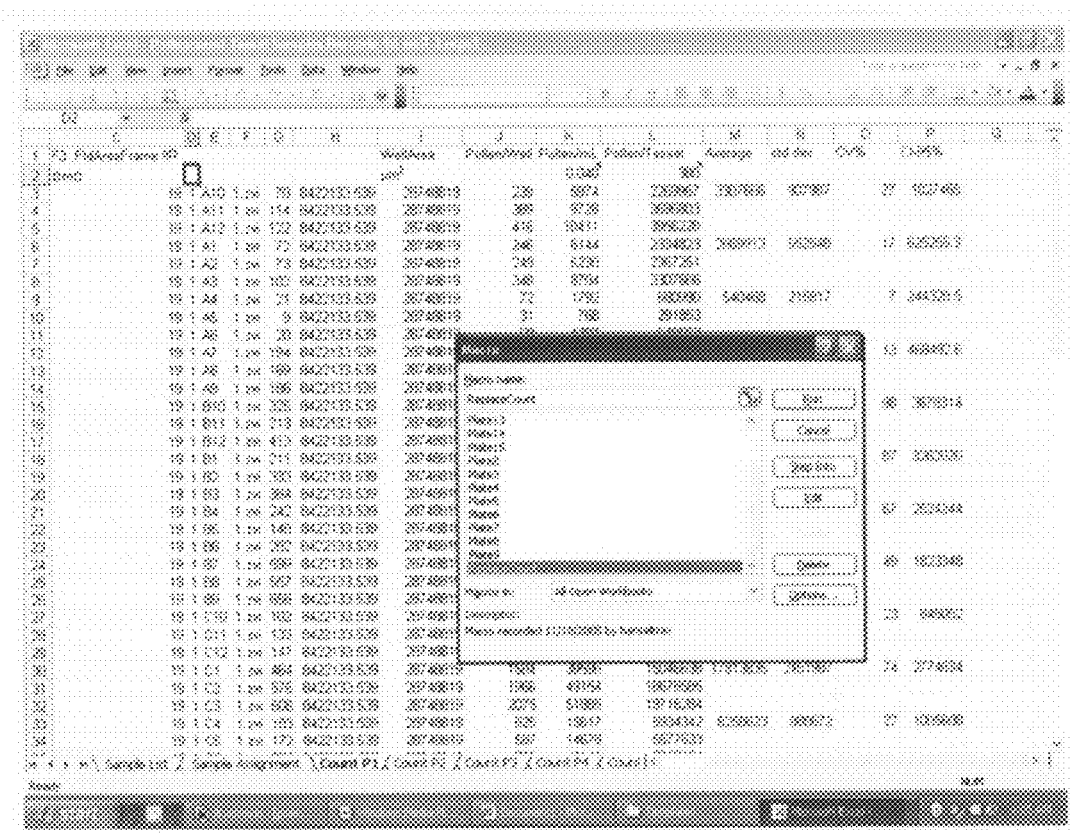
Fig.10.15

Error bars represent standard deviation of the mean.

METHOD AND APPARATUS OF HIGH-THROUGHPUT POLLEN EXTRACTION, COUNTING, AND USE OF COUNTED POLLEN FOR CHARACTERIZING A PLANT

I. BACKGROUND OF INVENTION

A. Field of the Invention

The present invention relates to quantifying pollen from a plant or genotype of plant, or different plants or genotypes of a plant, and in particular to apparatus and methods to assist in efficient and accurate pollen quantification, as well as subsequent beneficial use of pollen count for such things as, for example, characterizing a plant or its genotype or determining if a plant or its genotype has desirable traits or characteristics.

B. Problems in the Art

Pollen production is a key aspect of the ability of pollen to move to and fertilize the female parts of a plant. Likelihood for successful fertilization can increase with increasing levels of pollen production from a plant. The ability to accurately measure or estimate pollen production of a single plant can be used to provide beneficial insights to maximize pollen production for the plant. It can also be used to compare plants or varieties of plants. Still further, it can be useful to evaluate how genetics and/or environment effect pollen production, genetic and trait purity, and seed yield.

Attempts have been made to quantify the amount of pollen produced from a plant. However, several factors make accurate quantification difficult.

First, the capture of all pollen from a plant is problematic. Pollen are microscopic in size. It is light enough to be wind-blown or carried by insects. In corn, for example, pollen microsporogenesis occurs at different times in different parts of the tassel. These areas correspond to the parts of the tassel that shed at different times. This can indicate that, while some pollen is shedding from a tassel, other pollen might still be developing. Thus, it is possible that not all pollen in a tassel is available for capture at one time. One method uses sticky traps in the field to capture pollen. This method is based on collecting pollen available at silk level. However, this method does not capture all the pollen. Capturing total pollen shed from a tassel by placing a clear plastic bag over the growing tassel has been practiced. Although the bag allowed for gas exchange, concerns exist about stress effects imposed upon the tassel. With this technique, pollen is also captured post-shed. Other methods to capture pollen within a field have been devised but do not measure on a per tassel basis and are not conducive to small plot studies. A method that avoids some of these problems is the measurement of tassel weight difference between pre and post shed tassels. The difference in weight is an estimate of pollen shed from the tassel. This weight comparison has been used to determine the pollen production ability of an inbred parent corn plant. However, this technique is statistically variable and requires two, separated-in-time measurements. Furthermore, tassel parts also fall from the tassel before the post-shed tassels are collected. This may affect accuracy of estimation of the amount of pollen the tassel produces.

Second, if pre-shed pollen is to be quantified, extraction or separation of pre-shed pollen from its plant can be quite difficult. In the case of corn, the pollen is carried in anthers on the tassel. It is impractical to separate by hand. A variety of mechanized (e.g. dry grinding) and chemical methods have been tried, but have not been found satisfactory. Most tend to be time-consuming. Some damage the pollen. Many are not effective to separate all the pollen from debris or plant material. Some equipment is not properly designed for small particles leading to pollen escape or is difficult and impractical to clean between samples leading to sample to sample contamination.

Third, even if captured, the small size of most pollen (e.g. for corn roughly 60 to 105 µm in diameter), and prolific production (e.g. for corn roughly 0.5-25 million grains per tassel), have hindered efforts to efficiently or effectively count pollen. The pollen's small size defies unaided manual counting, while the large volume of pollen requires counting samples of the pollen and then estimating total pollen of the tassel or plant. Several methods have been utilized including visual counts, the use of the electrical charge properties of pollen, and the use of fluorescence properties of pollen. For example, a widely used test to attempt to determine pollen production ability of a corn plant uses visual estimation of tassel size to predict potential pollen production. Although this provides a rapid evaluation of pollen production ability, it is not quantitative. Another relatively recent method collects post-shed pollen by placing a bag over the tassel and counts the pollen using the Coulter principle technology to count and size particles (e.g. Coulter Multisizer brand). While the method appears to relatively quickly count a relatively large sub sample of pollen grains, and attempts to be quantitative, it is extremely labor intensive, time consuming, and may underestimate pollen production ability of genotypes that are responsive to heat stress. Therefore, known methods of estimating pollen production ability of corn plants based on these techniques reveal room for improvement. Also, known pollen counting methods tend to be time-consuming or of insufficient accuracy. Efforts to use such methods as quantification of sporopollenin, as well as many other attempts to determine pollen amount, have not provided good results.

Thus, there is a need for a faster, higher through-put (average time per count), efficient, and accurate method for a pollen count assay. There is a need for a quantitative, accurate, quick, highly reliable and reproducible way of extracting pollen grains from corn and other plants. There is also a need for a quantitative, accurate, quick, highly reliable and reproducible way of counting pollen grains from corn and other plants, whether pre- or post-shed. Likewise, there is a need for an improved method to characterize pollen production ability, compare pollen production between plants or varieties of plants, evaluate environmental or cultural practices, and/or evaluate plants or varieties of plants relative to their traits or characteristics and for further use, or not, in commercial production or research and development, as a few examples.

II. SUMMARY OF THE INVENTION

According to one aspect of the invention, pollen is separated from its plant by blending the plant with a liquid in a blender. Pollen is extracted from the liquid/plant suspension through a filter or strainer sized to pass relevant pollen grains.

According to another aspect of the invention, the separation and extraction steps can occur essentially in one-step to save time. The extraction can take place while the blender is operating to promote a more representative sample.

A further aspect of the invention includes a high throughput system for quantifying pollen. A sample of pollen is suspended in a liquid. The sample is placed in isolation and pollen in the sample is encouraged to distribute evenly in a plane. An image taken essentially orthogonal to the plane, and focused at or near the plane, is analyzed with image measurement software pre-programmed to recognize and count, in camera space, objects indicative of a pollen grain. The images of multiple sub samples can be taken efficiently and sequentially, and stored. Image analysis can also occur efficiently. This can result in relatively high throughput of multiple samples compared to prior methods.

A further aspect of the invention includes a combination of the (a) pollen separation/extraction and (b) the pollen counting aspects discussed above. The combination is efficient, conducive to high throughput and accuracy, and can be substantially automated from collection of pollen to its quantification.

A further aspect of the invention comprises accurate and reliable determination of the number of pollen grains for selection purposes in plant breeding, genetic advancement, or crop production, or to identify molecular markers associated with pollen production and tassel components. Another aspect using pollen quantification is to assess the impact of cultural and environmental factors on pollen production. It can also be used to identify plants or varieties of plants with desirable traits or characteristics for commercial or research purposes. For example, the invention allows researchers to quickly extract pollen from pre-shed tassels of maize and quantitatively determine the number of pollen grains per tassel. This information can be used to determine the ability of corn parent lines to be males in commercial seed production or can be used as phenotypic information to search for molecular markers for pollen production. This information can also be used to determine blend ratios of male-sterile and male-fertile hybrid seed so that adequate quantities of pollen are present in commercial hybrid grain production fields. In addition, this methodology may be adapted to quantify pollen production ability of male plants in commercial seed production of other hybrid crops such as sorghum, rice, and canola. An adapted version of this method could be used to quantify pollen production of both crop and non-crop species for assessment and characterization of environmental, cultural, and breeding effects.

III. BRIEF DESCRIPTION OF THE DRAWINGS

Figure 8:
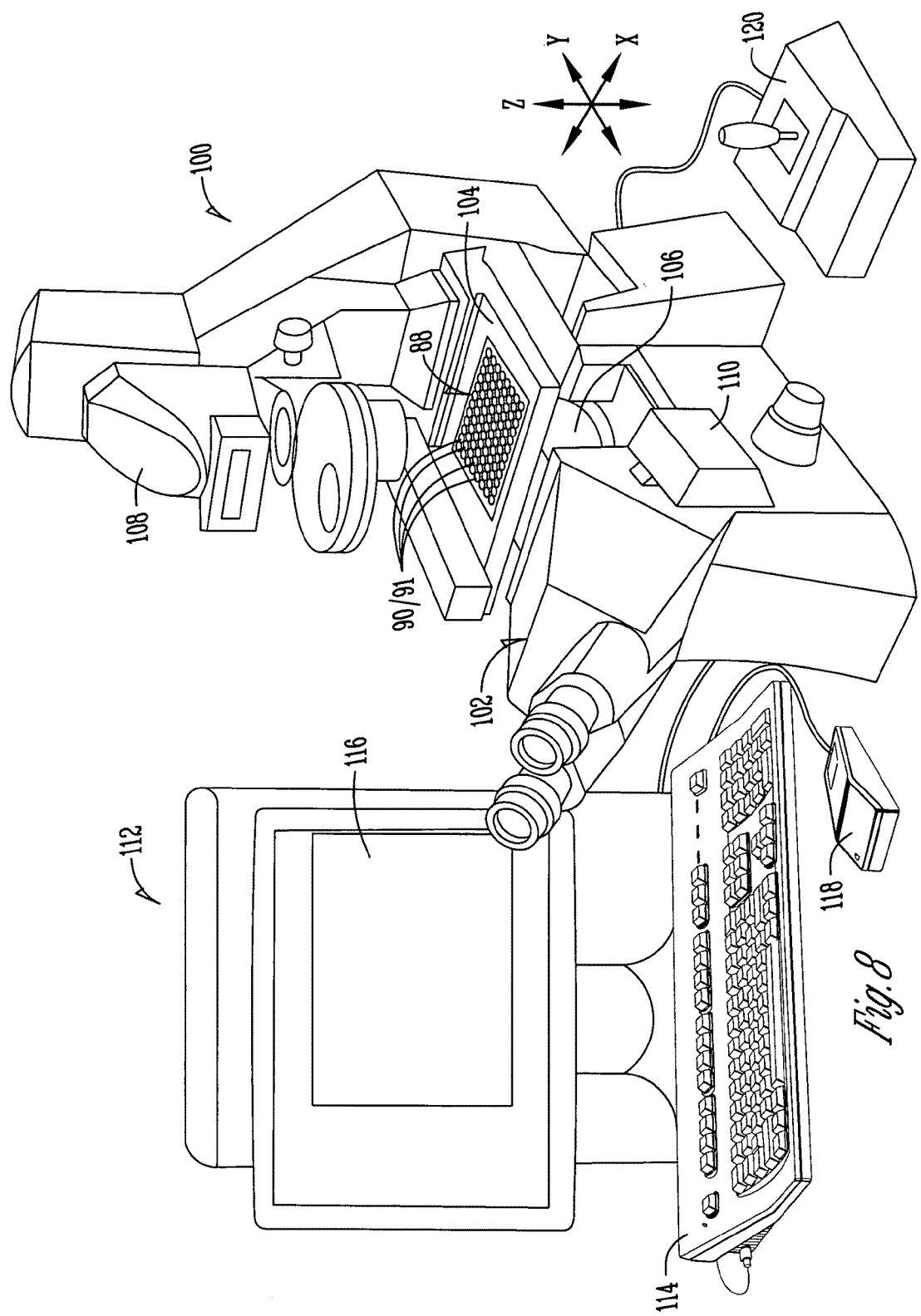
FIG. 8 is a perspective view of an imaging station with sub samples in the multiwell plate of FIG. 7 being sequentially imaged through a microscope.
Figure 9:
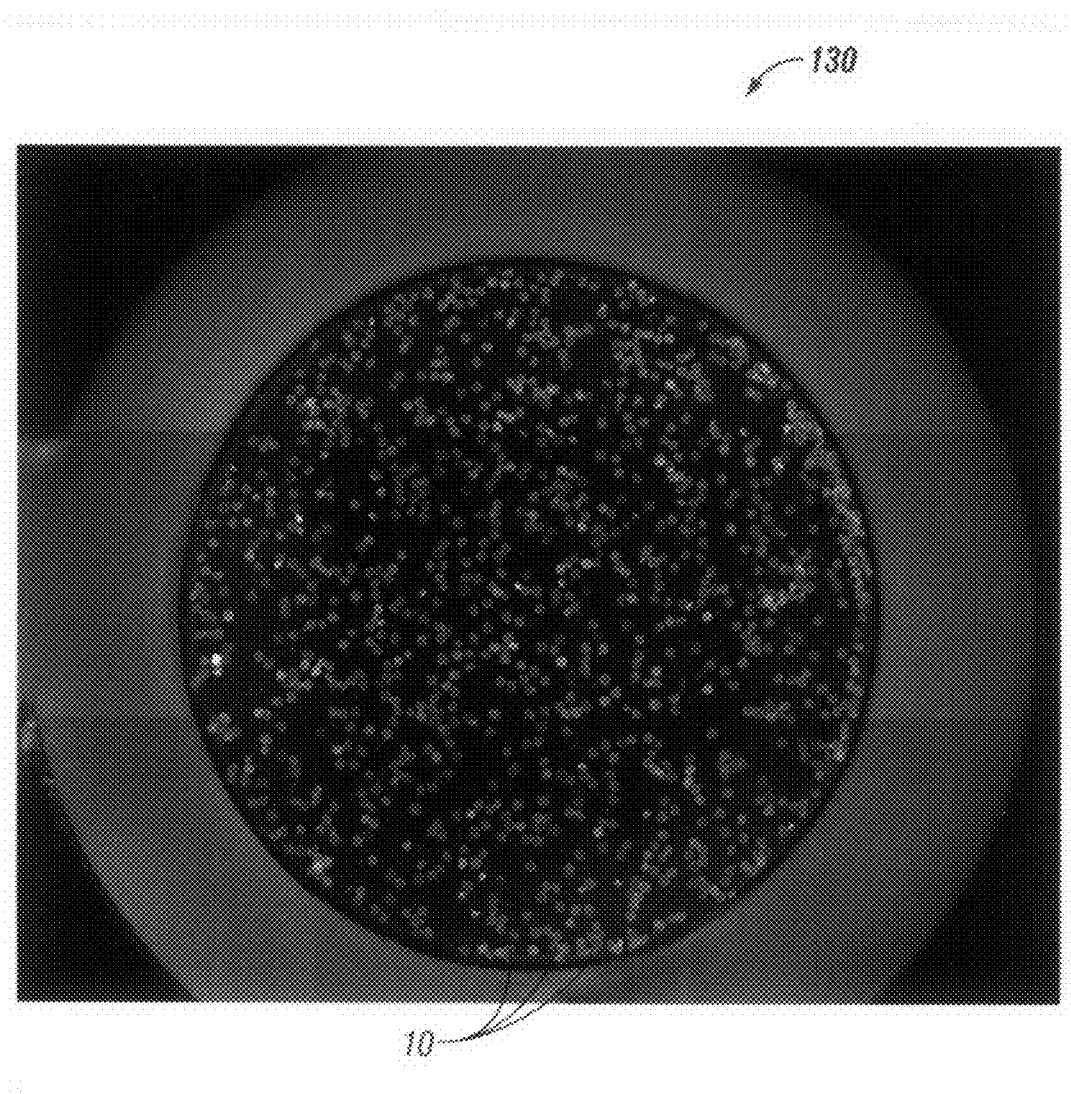
FIG. 9 is a picture of an image of corn pollen of a sub sample in a well of the plate of FIG. 7 through the microscope of FIG. 8.

FIGS. 10.1 to 10.17 are computer display screens which illustrate aspects and functions of programmable image analysis software that can be used to recognize and quantify pollen in the image of FIG. 9 with the imaging station of FIG. 8.

Figure 11:
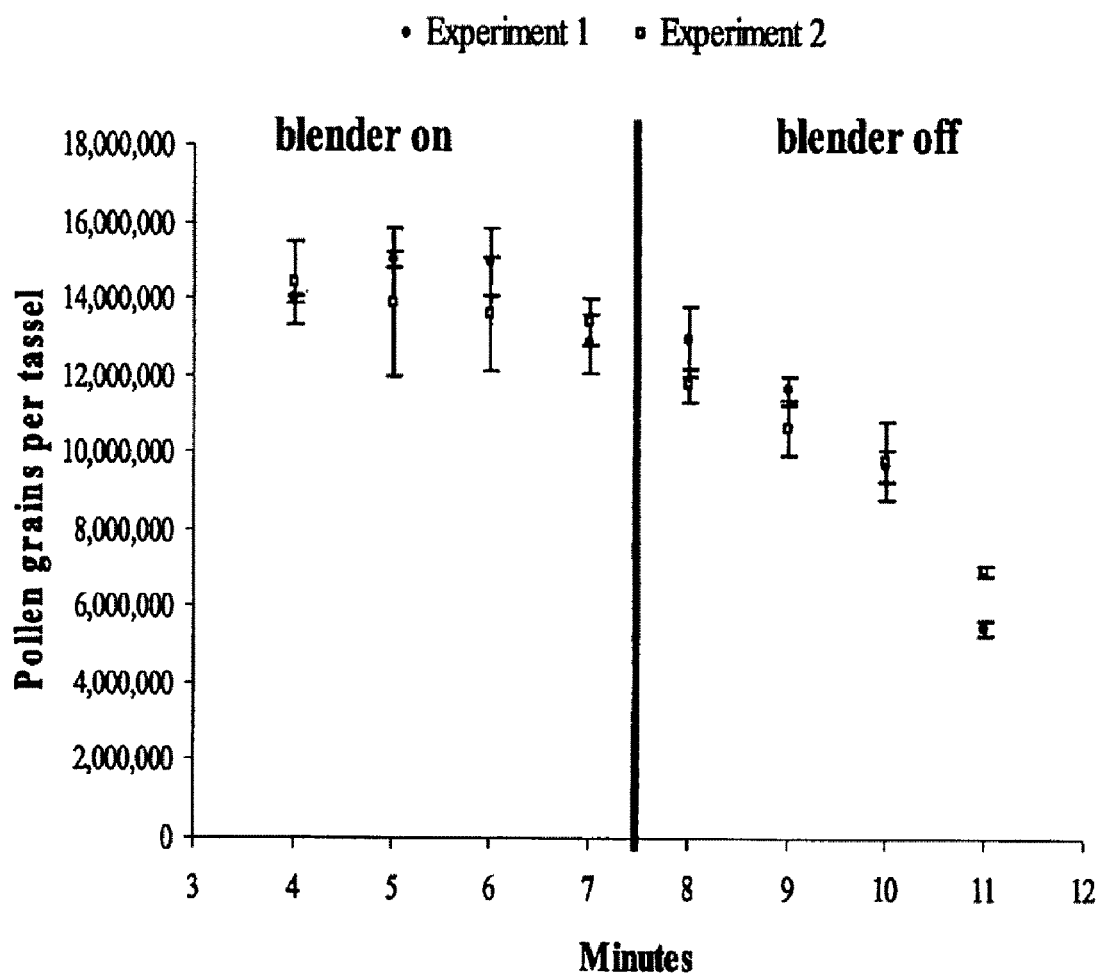

FIG. 11 is a graph of tests demonstrating better quantification of pollen when the sample is extracted from a running blender, as opposed to after it is stopped.

Figure 12:
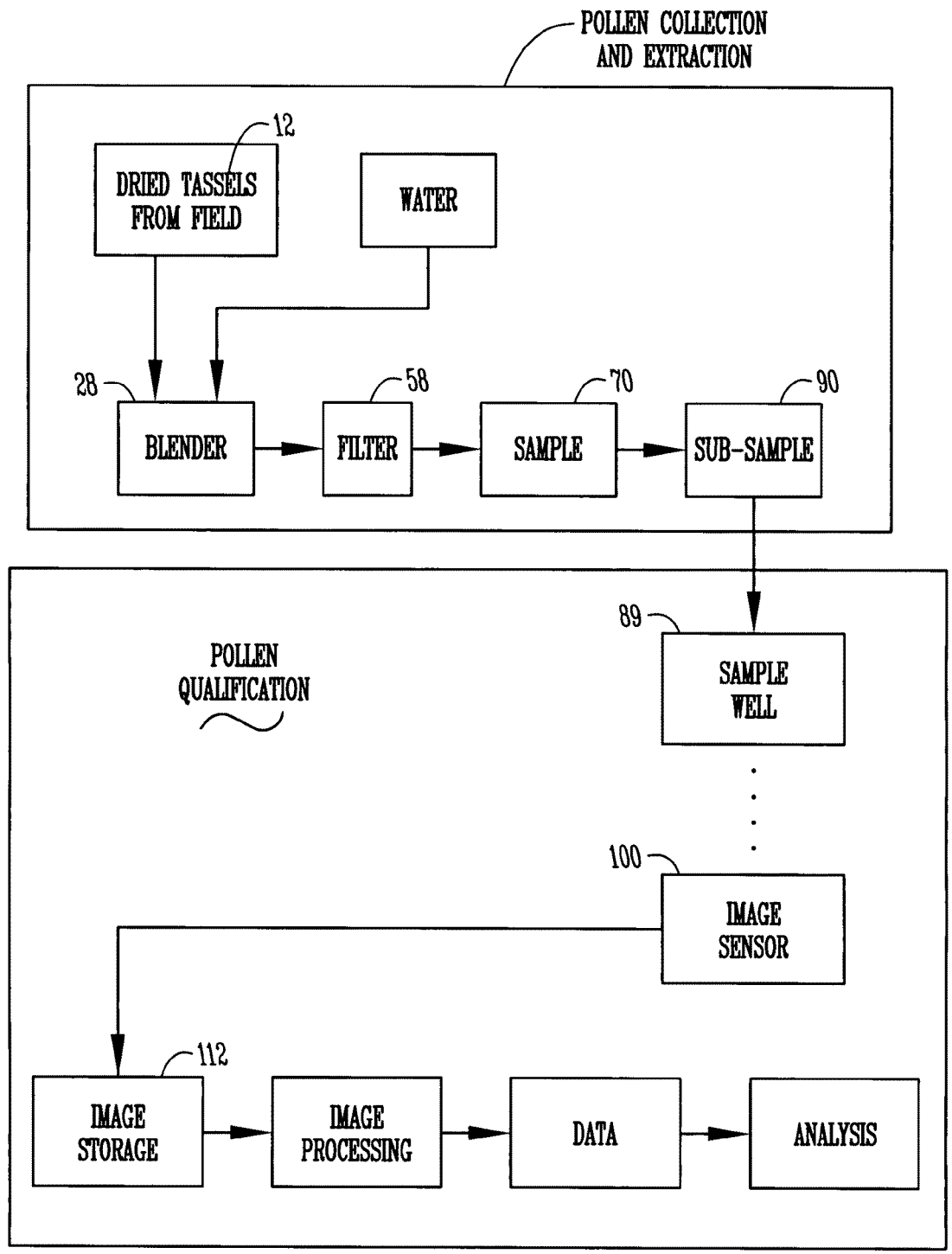

FIG. 12 is a block diagram illustrating a system of components, and their interaction, according to one aspect of the invention.

IV. DETAILED DESCRIPTION

A. Overview

For a better understanding of the invention and its various aspects, an example will now be described in detail. It is to be understood that the invention can take other forms and embodiments, and is not limited by these examples.

Reference will be made from time to time to the drawings identified in the preceding section. The drawings also assist in an understanding of the invention through the examples they illustrate. Reference numbers are used to indicate certain parts or locations in the drawings. The same reference numbers will indicate the same part or location in the drawings unless otherwise indicated.

B. Context of Example

The following description will be in the context of maize (corn), and with respect to the goal of obtaining a quantification of pollen per plant to make decisions about the value of reproducing the plant for production or for research purposes. However, it is to be understood that aspects of the described example can be applied to other uses, as well as to other plants, to pollen of other plants, and even to non-pollen particles.

C. Method

Figure 1:
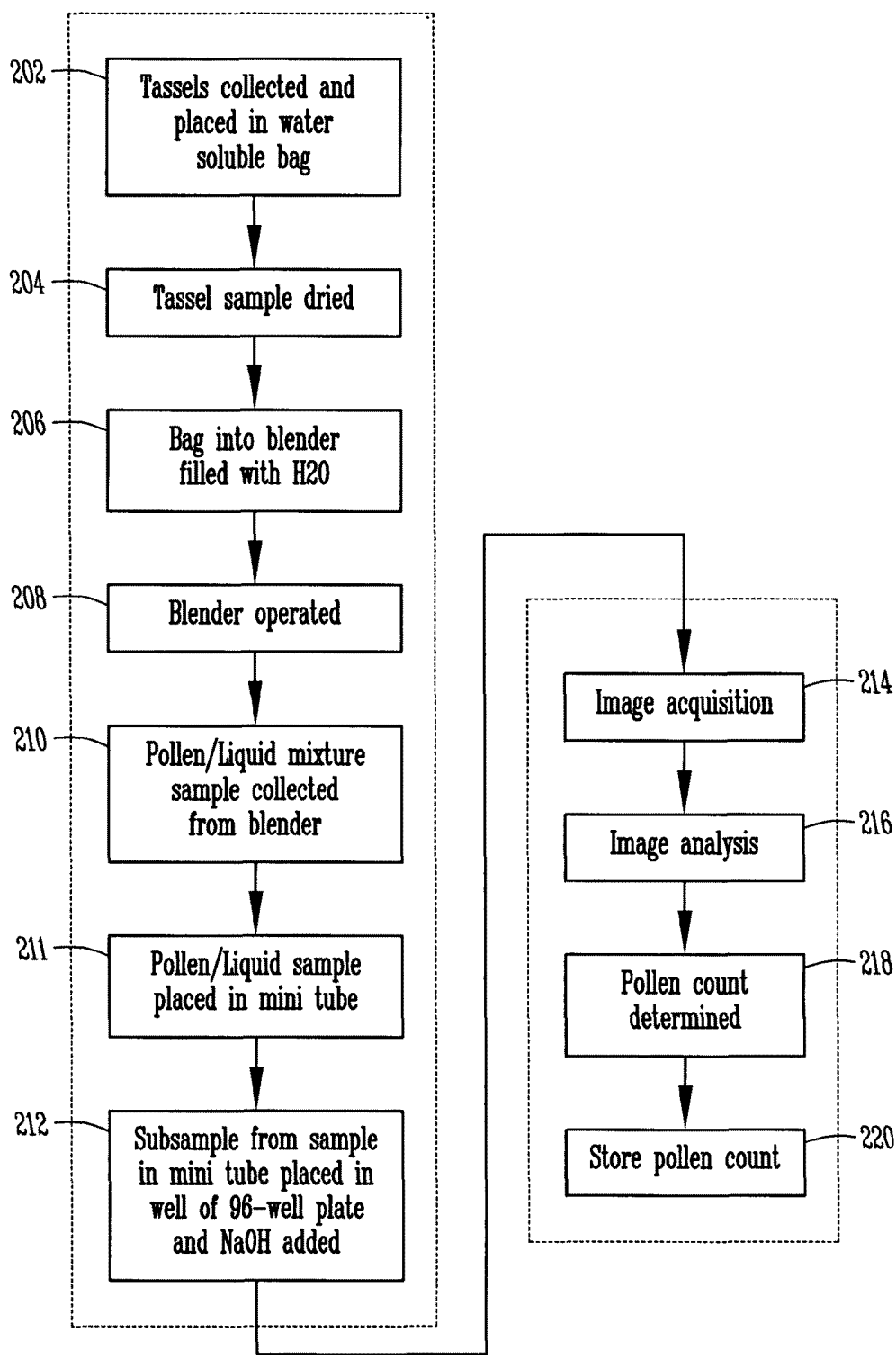
FIG. 1 is a flow chart of a method according to one aspect of the present invention.

FIG. 1 outlines a method (referred to generally as method 200) of extracting maize pollen from its carrier parts of the maize plant. Method 200 also outlines a method of quantifying that extracted pollen. These steps can be applied in an analogous manner to extracting pollen from other plants. Certain of the method procedures can be applied in an analogous manner to non-pollen particles.

1. Steps:

a) Pollen Collection

A pre-determined number of corn tassels (e.g. 1 to 5), with pre-shed pollen intact, are cut or otherwise separated from the plant (FIG. 1, step 202), e.g., at the beginning of or just prior to anthesis. The worker has a priori knowledge of the identity of the plant or plants, and maintains a correlation of that identity with the tassel or tassels that are collected.

Figure 2:
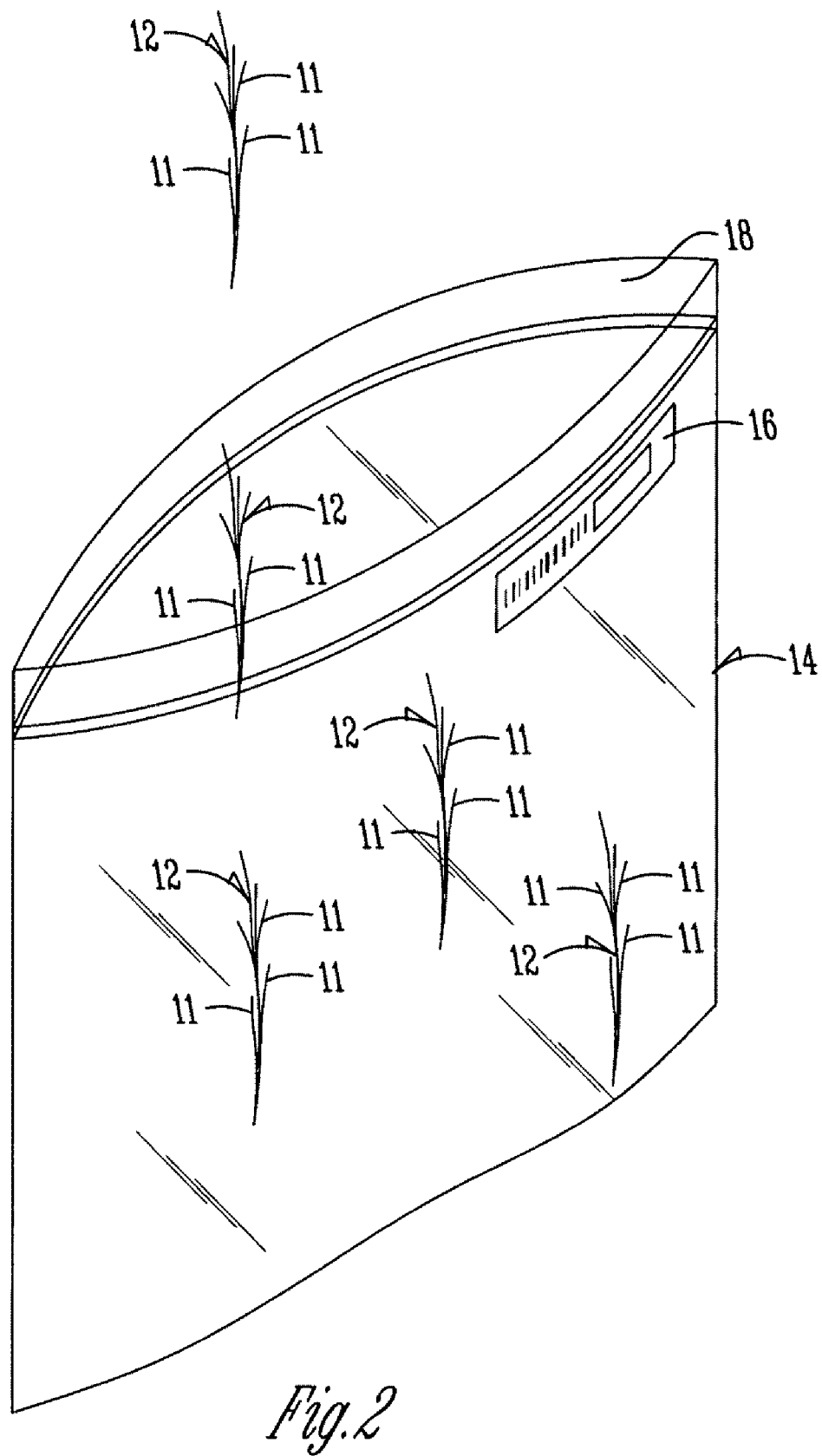
FIG. 2 is a diagrammatic illustration of an optional bag to store and transport corn tassels from a growing location to a pollen extraction and/or counting location.

One collection method places the tassel(s) 12, with pollen 10 intact in anthers 11, in a water-soluble bag 14 (see FIG. 2). A label 16 can include a bar code or other indicia from which identity of the source of the tassel(s) 12 can be derived. Bag 14 has a closure means 18 to retain tassel 12 for storage or transport. If a bag 14 is not used, some method of maintaining correlation of identity of the tassel(s) 12 is used.

b) Extraction

Figure 3:
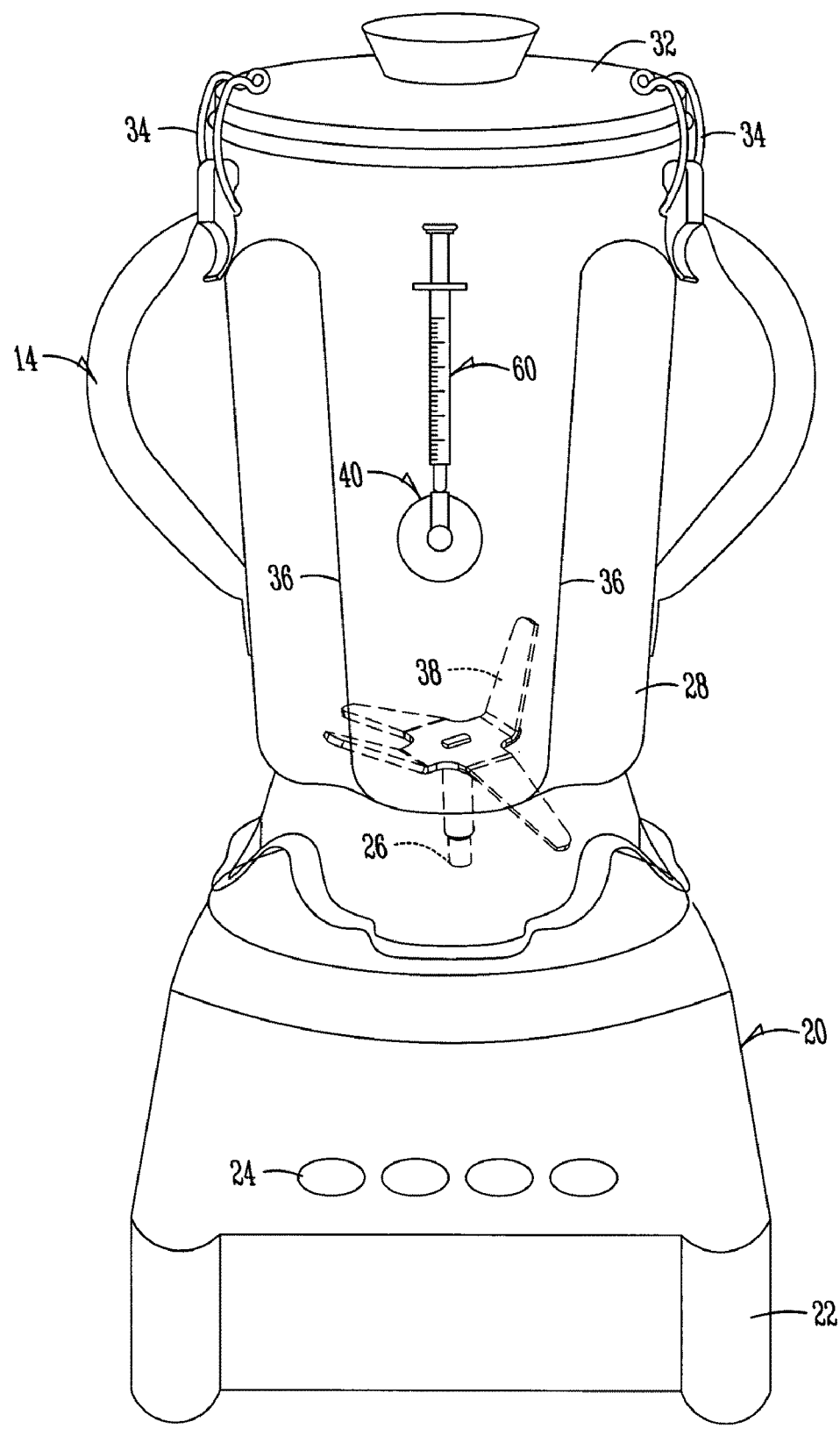
FIG. 3 is a front elevation view of a blender, a blender container, and a pollen extraction assembly installed on the blender container.

Pollen is extracted from tassel(s) 12 in water using a blender (FIG. 3). Prior to this, tassel(s) 12 is/are dried (step 204). Bag 14 is air permeable, allowing air drying to occur without removing tassel(s) 12 from bag 14. For example, the bags can be placed in an air flow of around 60 degrees C. for a sufficient time to dry them until they are brittle. Dry tassels allow for storage and transportation. Drying pollen also improves the integrity of pollen during grinding by minimizing, for example, pollen bursting when in contact with water. Grinding in liquid or liquid blending has been found to be conducive for pollen escape from the anthers by breaking the wet anthers. The anthers are cut up to expose the pollen. The agitation in the liquid and around the container encourage separation of the pollen grains from the anther materials. The drying and liquid has been found to promote separation, as opposed to clumping together, of individual pollen grains and suspend them in the liquid. This all promotes a more homogeneous mixture.

Figure 4:
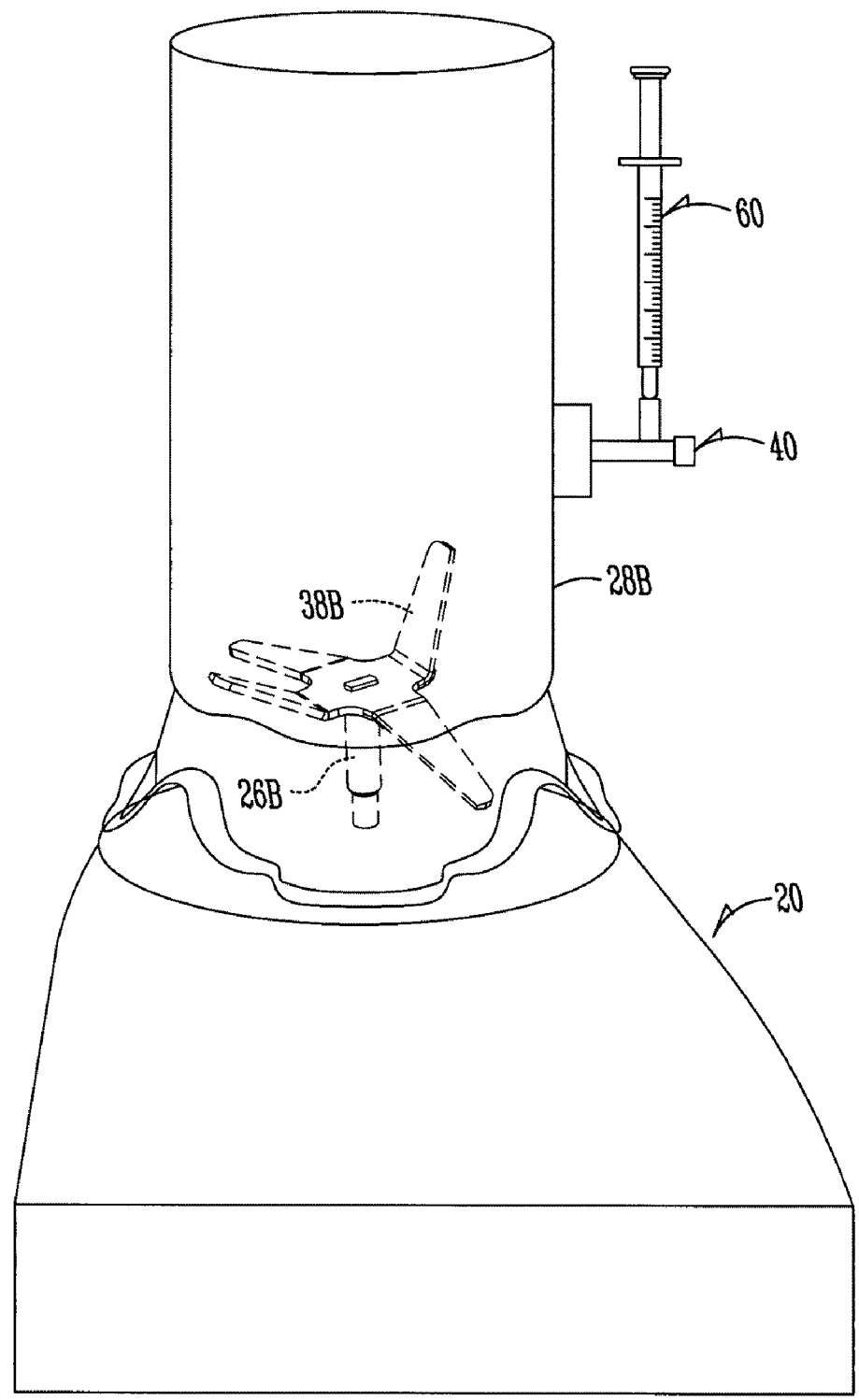
FIG. 4 is a perspective view of a smaller alternative embodiment of a blender container with pollen extraction assembly to that of FIG. 3.
Figure 5A:
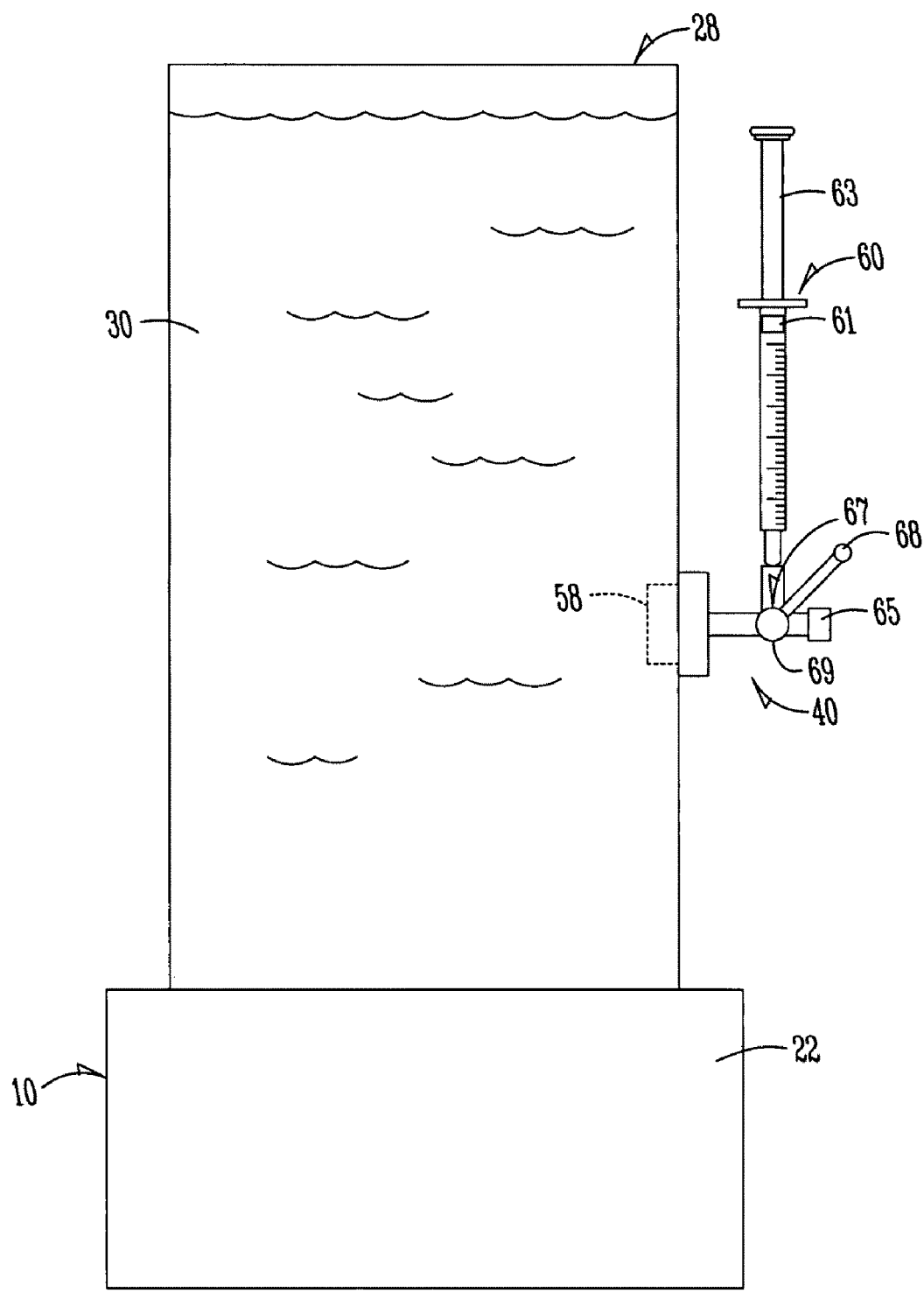
FIG. 5A is a side elevation diagrammatic illustration of the pollen extraction assembly of FIGS. 3 and 4 installed on a blender container.
Figure 5B:
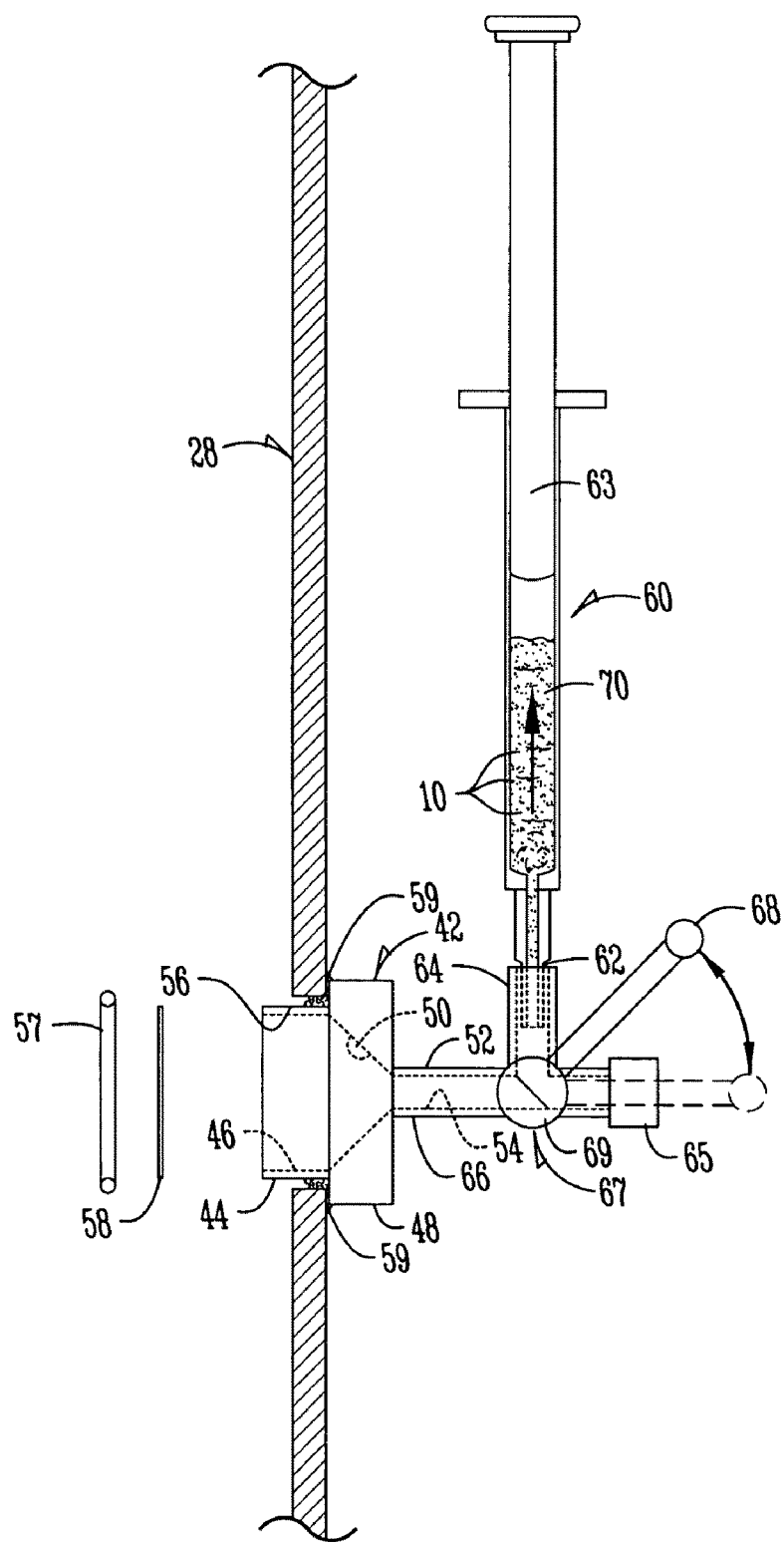
FIG. 5B is an enlarged, partially sectional, partially exploded view of the pollen extraction assembly of FIG. 5A.

Bagged dried tassel(s) 12 is/are placed into blender container 28 (see FIGS. 4, 5A, and 6), which is filled with water (step 206). Water is inexpensive, easily available, and environmentally safe. Bag 14 is water soluble. This allows it to be placed directly into the water in the blender, and eliminates having to remove the tassels from the bag, which could effect quantification as some pollen could stick to the bag or fall out if handled and transferred from bag 14.

The bagged tassel(s) 12 is/are blended in the water (step 208) for a period of time and at a blender speed designed to separate pollen 10 from anthers of tassel(s) 12. This creates what will be called a tassel matrix 30 of liquid and solids. Bag 14 dissolves or otherwise breaks down during blending and releases the tassels into the liquid matrix 30. An anti-foaming agent can be added to the tassel matrix to deter foaming in the matrix caused by chemical make up of the bag.

The matrix 30 is perturbed by the action of the blender blade, the geometry of the inside wall of the blender jar or container 28, and comminution of the tassels parts and container wall. For example, jar 28 can have portions extending radially inward. The liquid (water) is used to move the solids (tassels 12) around the jar 28 and bring that matrix in contact with the sides of jar 28 and the blender blade. The whirlpool-like fluid movement brings solids from the top to the bottom (the location of blade(s) 38) of the blender jar 28. High-powered blenders are capable of cutting, grinding, or milling action on the solids in the matrix, as well as circulating the matrix in jar 28. It has been found that this action, in water, basically breaks into smaller pieces the non-pollen plant parts, and releases or separates most, if not all, pollen grains from anthers and other tassel material but does not break or cut apart pollen grains. The whole grains of pollen are therefore loose and suspended in the matrix with other broken up plant parts. Empirical testing can establish blender speed and length of blender motor operation for satisfactory pollen separation.

It has been found that blending of the tassel matrix results in the rapid break-up of a dried tassel(s) and simultaneous separation of whole pollen grains from tassel parts. Many types of tassel destruction techniques were tried but quantitative recovery of pollen is achieved after tassels and pollen grains have been dried and when liquid is utilized to extract pollen from anthers and other tassel parts. Similar action and forces could be used for other types of plants with pollen carried by or in plant parts.

After sufficient blending has occurred, an aliquot (a small sample) of the blended tassel matrix is extracted using an internal filtration or strainer device (step 210), which is selected to allow passage of liquid and particles in the normal size range of pollen to be counted. The normal size distribution of corn pollen is well known in the art, as are size distributions for pollen of other species. Alternatively, those skilled in the art could use conventional methods to measure plant pollen and select an appropriate filter. One example of a filter passes all or almost all pollen to be counted, but blocks or strains out solids that are just above the upper limit of sizes the filter passes. Doing so tends to block or strain out most non-pollen plant parts, which means further filtering, straining, cleaning, or purifying of the pollen may not be needed.

It has been found to be advantageous to extract the aliquot or sample while the blender is running as it tends to produce a statistically more accurate sample. If the blender is turned off before sampling, pollen could settle towards the bottom and affect whether the sample is representative. FIG. 11 shows results of tests which demonstrate sample extraction while the blender is running that are repeatable and reproducible, and thus reliable, samples for pollen quantification. Experiment 1 of FIG. 11 utilized blender mixing and extraction while running. Experiment 2 of FIG. 11 shows extraction after the blender is turned off.

Blending the liquid matrix both chops and suspends the solids in the liquid. Extraction while the liquid and suspended solids are moving, and cleaning the sample while extracting, provides a sample of pollen that can be counted. No further cleaning or filtering is needed. This promotes quicker throughput of samples.

The simultaneous filtration of pollen, through an appropriately mesh size sieve, from suspended tassel parts in the liquid solution as the tassel is being destroyed in the blender, dramatically increases the speed of the entire isolation process. The mesh sieve is substantially self-cleaning because of movement of tassel matrix laterally across it during blender operation.

Therefore, method 200 outlines a process that has been discovered to satisfactorily speed up the separation of pre-shed pollen from its plant, and extract a statistically representative sample of the pollen. For corn pollen and conventional commercial laboratory grade blenders, blender operation at relatively high speeds for between two to four minutes has been found sufficient. Thus, a representative sample from one or more tassels can be obtained within no more than a few minutes or so.

The blending/mixing grinds the tassels and results in a relatively homogenous suspension. Pollen is relatively resilient and stays intact. The other tassel parts are basically destroyed, but for the most part are larger than the sieve openings and do not pass out of the blender container when a sample is taken or are ground to cellular components, a size significantly smaller than pollen.

c) Quantification

Method 200 also provides a process for obtaining a statistically acceptable quantification of pollen, once it is collected. It is to be noted that the quantification process can be applied to pollen obtained from the pollen extraction process of steps 202-210, but also can be applied to pollen that has been collected by other pre-shed or post-shed methods. Quantification can be applied to most, if not all, pollen. It can be applied to non-pollen particles also.

The sample (or aliquot) extracted from the tassel matrix (step 210) is placed into a mini tube vial (step 211), by filling the vial up to an indicator or indicia of a standardized volume for each vial (e.g. a 0.8 mL level). A sub sample from the mini tube vial is placed into a well of the 96 well plate (step 212). An image or images of each well is taken (step 214). In method 200, a sub sample from the mini tube vial (step 212) is quantitatively transferred into a well of a multiwell plate (e.g. ninety-six well plate 88 in FIG. 7) to provide an isolation compartment of known volume with a transparent flat bottom of known area. Therefore, essentially a sub sample of the sample of the blender matrix is placed in a well and at least a portion of the well is imaged.

For corn pollen, a measured amount of sodium hydroxide (NaOH) is also added to the well (step 212), as it has been found effective to enhance contrast of corn pollen from the background, the liquid fraction, and any debris or plant material, when the well is illuminated by appropriate wavelength light. The addition of NaOH (a pre-imaging soak) causes the isolated pollen to fluoresce more uniformly and reduces background fluorescence of non pollen debris, which uniquely distinguishes the pollen from other tassel parts present in the liquid. This allows the imaging analysis technique to be more reliable in accuracy and precision. It has been found to improve the imaging analysis software's ability to count fluorescing objects (e.g. pollen grains). One possible alternative to NaOH is potassium hydroxide. It has been found that pre-imaging soaking for some time (e.g. a few hours) improves the NaOH effects.

An image of the well containing the sub sample and NaOH mixture is acquired (step 214) using a commercially available imaging station (e.g. AxioObserver inverted research microscope with motorized stage having three dimensional controllable movement, filtered fluorescence lighting, and digital imaging functions from Carl Zeiss MicroImaging GmbH, Göttingen, GERMANY) through a microscope while illuminating the sample with light of wavelength to cause the appropriate fluorescence for higher contrast of pollen. Any of a number of commercially available imaging systems can be used. Image analysis software compatible with the images can be used to identify and count what appear to be pollen grains in the images.

It has been found advantageous to allow the sub sample and NaOH mixture to sit for a time (e.g. a few minutes) to allow the pollen grains to settle to the bottom of the transparent well. This has been found to promote better accuracy of counts, because most, if not all, of the pollen would fall to the bottom of the container of the sample, and thus reside in a single image plane of the camera, and more likely present better in the image.

Commercially available software (e.g. AxioVision from Carl Zeiss MicroImaging GmbH) is used to analyze the image of the well (step 216). The software autonomously counts the number of objects that are of pollen grain dimension(s) and florescence (step 218). These parameters are programmed into the system by the user. Based on the aliquot amount and the object count, the number of pollen grains per tassel is determined. The software does allow, however, manual override or revision of the count.

The count is stored in a database (step 220) that correlates the count to the identity of the sub sample, which is also correlated back to the identity of the plant(s) from which the pollen came. By straight forward calculations, the count from the imaging software for the sub sample can be used to derive a quantification of pollen for its whole tassel and/or for its whole plant.

Therefore, method 200 presents a process by which a statistically acceptable quantification of pollen from a tassel or tassels can be derived, whether pre-shed or post-shed. As can be appreciated by those skilled in the art, when combined with the extraction process (steps 202-210), the quantification (steps 212-218) can be done quite quickly, even for large numbers of samples. Thus, quantification of pollen can be accomplished at a relatively high throughput with good statistical accuracy on a tassel-by-tassel (or set of tassels by set of tassels) basis.

Moreover, the extraction process can be managed to successively extract a number of samples and prepare them for imaging and counting. The imaging and/or counting can occur right after sample extraction and/or at later times as is/are convenient. Method 200 therefore has good flexibility as to use and allocation of human and equipment resources.

Excellent correlations have been found using image analysis to count pollen grains for pollen counts across a wide range of genetics and relative maturities (see, e.g., Tables 1 and 2, infra). Accuracy to within one standard deviation has been found across a wide range of genetic and relative maturities. The method has also been found to be repeatable and reproducible, and therefore has high reliability.

Other measurements, such as pollen weight, protein content, starch content, or other quantitative measures, do not work as well. Other pollen counting techniques, such as devices utilizing the Coulter principle technology (e.g. Coulter Counter or Multisizer brand), do not work as accurately or as specifically as image analysis.

It has been found that method 200 is effective for pre-shed pollen quantification with field collection of the tassel prior to pollen shed. The less mature pollen grains which are of smaller diameter in the lowest branch than those at the midpoint of the main rachis have been found to be of sufficient size and maturity at the start of shed that they are counted. It has been found that virtually all pollen grains are of sufficient size and maturity a few days prior to shed, which facilitates efficient tassel collection. Method 200 has been found to be suitable for pollen quantification when tassels are collected prior to pollen dehiscence.

A liquid handling system 86 could be added to automate the addition of NaOH to the wells and to extract a sub sample from the mini tube vial 77 (see FIG. 6) containing the matrix aliquot for image analysis. Such liquid handling systems are commercially available (e.g. Biomek™ 3000 Laboratory Automated Workstation, Beckman Coulter, Inc., 4300 N. Harbor Boulevard, P.O. Box 3100 Fullerton, Calif. 92834-3100 USA; another possible example is a Janus or Evolution brand automated liquid handling systems with Platestak microplate handler and En Vision label reader from Perkin-Elmer, Waltham, Mass. USA) and can be programmed to conduct needed functions. Others, of course, are possible.

Method 200 can be used to determine the number of pollen grains in one tassel, a portion of a tassel, or up to 5 tassels or more simultaneously. Information gained can be used to determine the ability of a plant to produce pollen, impact of cultural or environmental factors on pollen production, and can assist in the search for molecular markers that are associated with pollen amounts and/or tassel components.

Used together (extraction method and quantification method), total time per sample can be on the order of five minutes. This represents a substantial decrease from other methods. It allows relatively high throughput of numerous samples. It is also labor saving and environmentally friendly.

D. Apparatus

Apparatus to practice of method 200 can include the following. A block diagram of the apparatus is set forth in FIG. 12 and reference to FIGS. 1-10 provide additional details.

1. Extraction a) Collection Bag

Collection bag 14 (FIG. 2) is air permeable and water soluble to allow tassel(s) 12 to be collected and retained, but also to be dried and placed directly in the water in blender jar 28 without having to remove them. Examples of material for bag 14 include water soluble film (e.g. Product #506 from Monosol, LLC of Merrillville, Ind. USA); or Elvanol® brand polyvinyl alcohol (PVOH, sometimes also referred to as PVA), water-soluble synthetic polymer from the DuPont company, Wilmington, Del. USA (has excellent film-forming, emulsifying, and adhesive properties, resistance to oil, grease and solvents, high tensile strength, flexibility, and high oxygen barrier)).

b) Blender

Blender 20 (FIG. 3) can be any of a number of commercially available types and models. Even home kitchen types could work. An example of a commercial grade model is Waring Heavy Duty Blender Model LBC15, four liter capacity, stainless steel container 28 with clamp-on lid 32 (Waring Laboratory Science, Torrington, Conn. USA). Manually selectable (from control panel 24) motor speeds include slow (16K RPM), medium (18K RPM), and high (20K RPM). High speed operation has been used. Slower speeds may also work, but may require more time of operation. As noted, sidewall 36 of container 28 has vertical indentations. Blades 38 extend into the bottom of container, 28.

FIG. 11 shows test results that demonstrate it has been found it may be advantageous that the blender be engaged (running) when obtaining a sub sample from the tassel matrix to accurately quantify pollen production of maize. Protocols (described below) for pollen extraction and quantification procedures were followed. In these experiments a sub sample was collected following protocol procedures at 4, 5, 6, and 7 minutes while the blender was engaged. After the 7 minute sub sample was collected, the blender was disengaged (turned off) and at 8, 9, 10, and 11 minutes a sub sample was collected following protocol procedures. Experiment 1 and 2 were conducted by two different individuals on two separate dates. These results indicate it may be advantageous that the blender be operating in order to collect repeatable and reproducible sub samples from the tassel matrix for pollen quantification.

Blender essentially wet grinds the tassels and water into a homogenous suspension. Importantly, the liquid moves the solids around the container 28 and into contact with the blades by whirlpool action, as it brings solids from top to bottom and repeats. It has been found that with blender 20, at least 2 minutes at high speed works. Operation for over seven minutes, and perhaps over four minutes, may not produce any better results. Empirical testing can establish appropriate length of time at a given speed. The general rule is that the blender should be operated to produce enough force for long enough to break up the tassel so pollen is released from the tassel.

When configured for operation, water is added to blender container 28. Water soluble bag 14, containing the tassel(s) 12) with pollen for quantification, is also added. Lid 32 is latched. Blender 20 is operated at a selected speed and time to produce the tassel matrix of water, tassel parts, and separated pollen. It has been found that 3000 mL of water works well if several tassels (e.g. five) are to be blended at once. A smaller container 28B (e.g. 1 L capacity) could be used for one tassel (see FIG. 4).

c) Sample Extraction Assembly

Container 28 (or 28B) is modified from its conventional form to add to it a sample extraction assembly 40 to remove an aliquot or sample of the tassel matrix. A hole 56 (e.g. 1 inch dia.) is machined or formed in the sidewall of blender container 28 at or near the positions shown in FIGS. 3, 4, or 5A (e.g. 6.25 in. above exterior base of blender container 28). Hole 56 is just slightly larger in diameter than the outside diameter of the externally threaded male portion 44 of the male half 42 of a conventional syringe type filter holder (e.g., stainless steel microsyringe filter holder catalogue number XX3002514, Millipore, Billerica, Mass., USA). Threaded male portion 44 is inserted through-hole 56, with the larger head portion 48 of male syringe filter holder part 42 on the external side of blender container 28. Adhesive (e.g. epoxy) 59 is used to secure the syringe filter holder part 42 in place on the blender container sidewall, as well as seal the opening or hole 56.

A stainless steel screen, strainer, or filter 58 (approximately 150 micron opening size) has a diameter than covers the internal end of part 44. It filters or strains out larger non-pollen solids but lets relevant pollen and liquid pass. A rubber or similar O-ring can be secured with an adhesive (e.g. a strong adhesive such as cyanoacrylate (sold under brand names Super Glue and Krazy Glue)) near the perimeter edge on one side of screen 58 to assist in its stability and structural robustness (see FIG. 5B). The other side of screen 58 is adhered (e.g. with Super Glue) to the open end of male part 44 of the filter holder half 42. The assembly 40 therefore presents a pathway through which tassel matrix 30 can be filtered and removed from blender container 28.

A three-way valve 67 (a "shut-off" valve) (e.g. Three-Way Valve, Fluoroware, Inc., Chaska, Minn. USA) is mounted on the Luer lock hub 52 of syringe filter holder 42 and sealingly secured in place. Valve 67 has an inlet tube 66 (with internal fluid pathway) which is the single inlet port to the valve and is in fluid communication with the internal fluid pathway 50/54 of syringe filter holder 42 (tube 66 sealingly connects over Luer lock hub 52). Valve 67 has a first outlet tube 64 (with internal fluid pathway) which has an open distal end into which can be mounted the tip 62 of a syringe 60. A second outlet port (65) is capped off (but could be used). As illustrated diagrammatically in FIG. 5B, lever 68 can be selectively manually moved between two extreme "closed" and "open" positions, which moves a valve element 69 to either close or open the fluid pathways between the (a) inlet port and the interior of blender container 28 and (b) the outlet ports of the valve (and thus syringe 60 at the distal open end of outlet tube 64).

To withdraw a sample of tassel matrix 30 from blender container 28, tip 62 is sealingly fit into outlet tube 64, syringe plunger 63 is moved towards syringe tip 62, and lever 68 of valve 67 moved to the open position. Because opening 56 in container 28 is below the top of tassel matrix 30, tassel matrix 30 would try to flow into extraction assembly 40 to syringe tip 62. However, screen 58 would filter or strain from the tassel matrix 30 anything that does not pass through its screen mesh size. In this case, the mesh size is selected to allow passage of relevant pollen. Because of the small size of such pollen, most of the solids that pass are pollen. Syringe plunger 63 would be moved away from tip 62 to draw a filtered sample of the tassel matrix into syringe 60. Syringe 60 could include a label 61 which could include identifying information of the sample.

An example of sample size would be from 0.5 to 3 mL. Thus, whether the tassel matrix 30 is 1 L or 3 L in volume, a sample 70 representing about 0.0167 to 0.1% of the starting volume is obtained with syringe 60, and it is filtered to contain predominantly pollen and water.

It has been found advantageous to extract the sample while blender 20 is running. The extraction method therefore allows for relatively quick and accurate separation of pollen from its plant, and extraction of a proportional sample. With appropriate cleaning to ensure no cross contamination, successive bags can be processed at quite high throughput.

Strainer screen 58 is substantially self-cleaning but blocks most non-pollen solids and lets most if not all relevant pollen through. By selection of the appropriate mesh size, no further filtering, cleaning, purifying of the sample is needed, which saves time. Under high speed operation with 3 L of water, blender 20 produces enough force and pressure that the filtered tassel matrix 30 flows through screen 58 and is available for sampling.

There is usually enough pressure that filtered matrix 30 flows right through to syringe 60 when valve 67 is opened. Optionally, if the cap on the other outlet (65) of valve 67 were removed, and the valve were opened, the filtered matrix would flow right out. This could be an alternative way to take a sample from blender container 28, while blender 20 is running. Other valving configurations which allow selective sample removal are; of course, possible.

d) Sample Organization and Storage

Once a sample of the matrix 30 is obtained, pollen in the sample can be quantified. Simple proportionality allows an estimation of total pollen from the tassel(s) from a quantification of pollen in the sample. As indicated, withdrawal while blending is occurring provides a statistically representative sample of total pollen in matrix 30 in blender container 28. Estimation of pollen in each tassel, if more than one was placed in matrix 30, would further include dividing the total pollen estimation by the number of tassels.

As can be appreciated by those skilled in the art, the pollen extraction method can provide relatively high throughput to obtain samples of pollen for quantification. Any of a number of quantification methods could be used once the pollen is separated from the plant.

Figure 6:
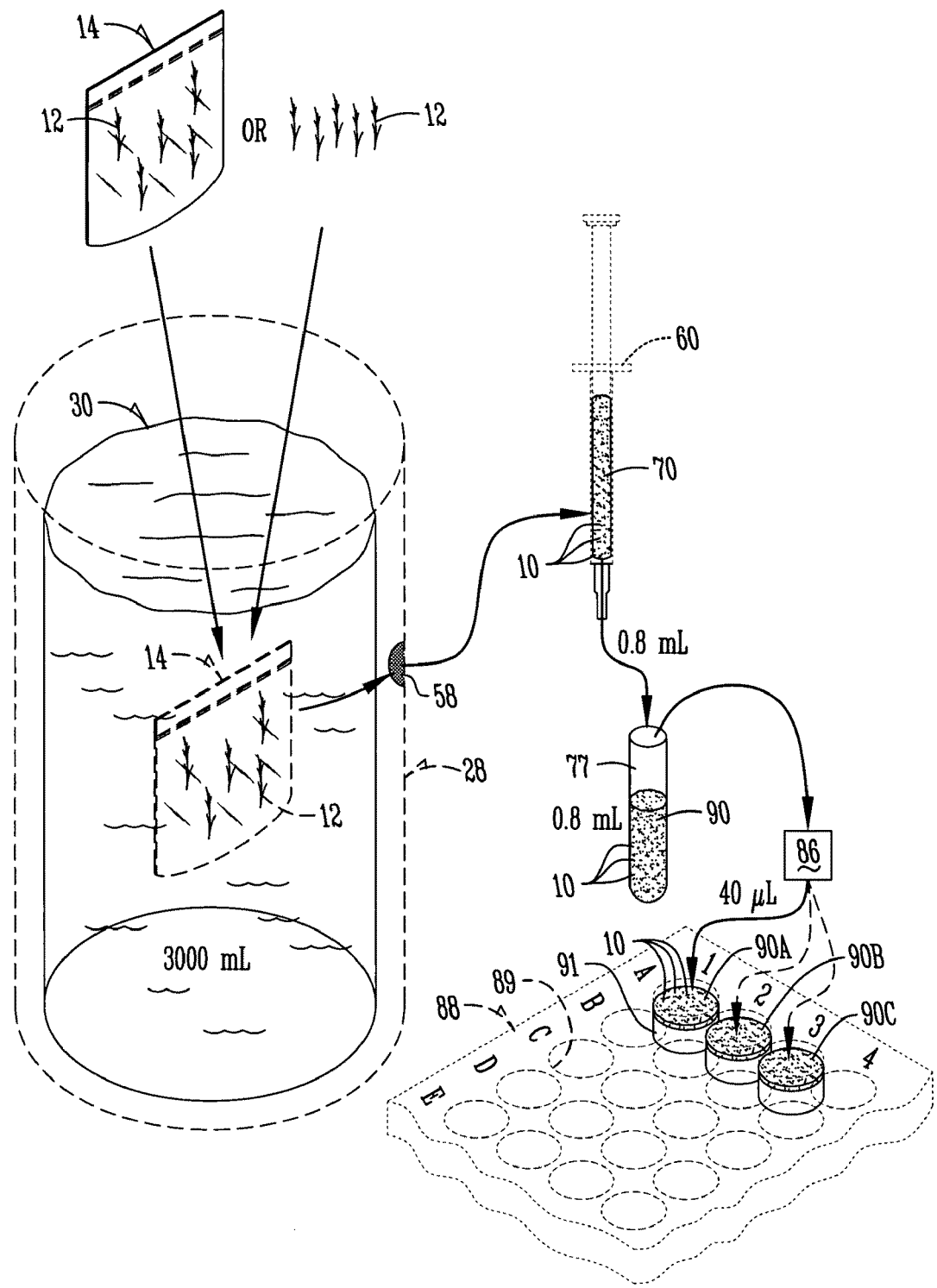
FIG. 6 is a diagrammatic illustration of a procedure for extracting a pollen sample from the blender container and placing a pollen sub sample into a well of an indexed 96 well plate.
Figure 7:
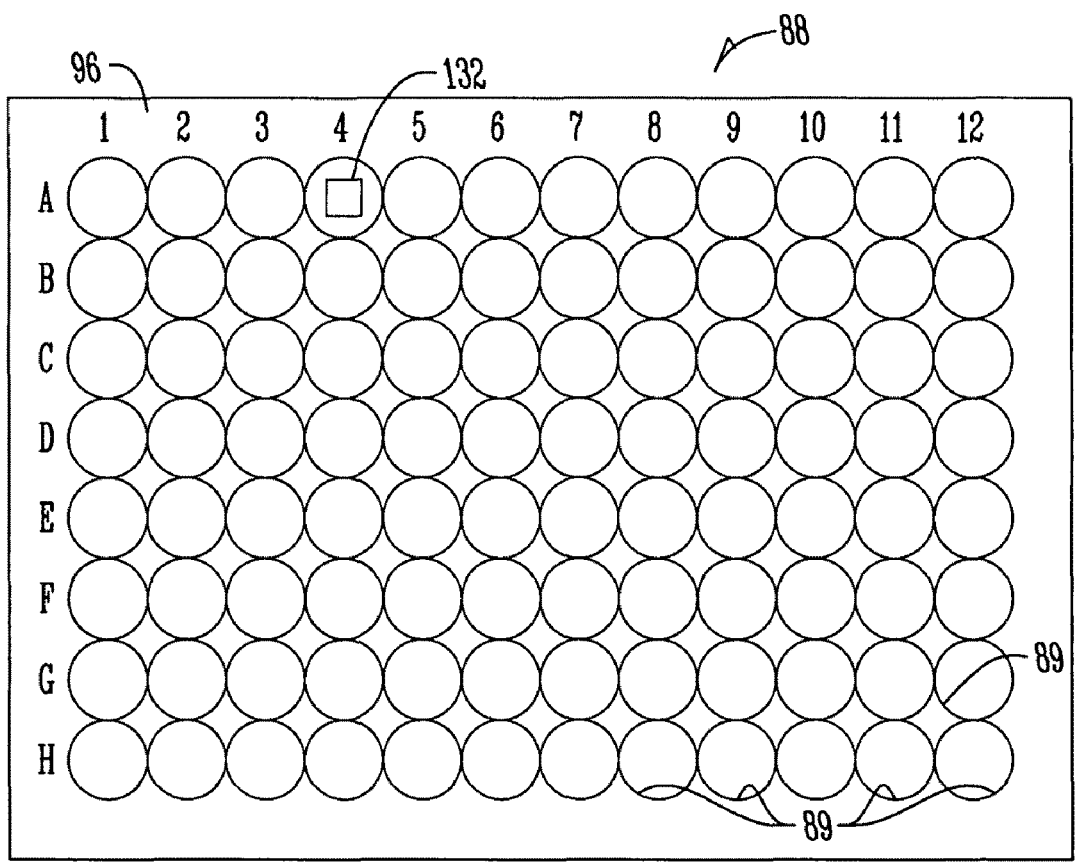
FIG. 7 is a top view of a 96 well plate for receiving and organizing sub samples in preparation for imaging at an imaging station.

There are ways in which a number of samples can be handled and organized in an efficient and orderly fashion. One way is illustrated in FIGS. 6 and 7. A multi-well tray 88 (here 96 wells arranged in eight rows A-H and twelve columns 1-12—see top view of FIG. 7) is a convenient way to store and maintain correlation of identity of multiple samples. A label (e.g. machine-readable label such as a bar code) could be placed on tray 88 and include identifying information about the tray and samples in the tray. An example is a conventional laboratory 96 well microtiter plate (e.g. from Wheaton Science Products, Millville N.J. USA). The volume of each well 89 of tray 88 could be large enough to hold a complete sample 70 extracted by syringe 60 as long as exact volume of sample 70 is known. On the other hand, it has been found that, at least with the pollen extraction method described above, a part (a sample 70, e.g., 0.8 mL) from the volume extracted by syringe 60 (e.g. 2 to 3 mL) could first be placed in an intermediate liquid container (e.g. a mini tube 77), and then a sub sample 90A (e.g. 40 μL (microliter)) from the mini tube 77 could be placed in a well 89 of tray 88 using either a liquid handling system or a pipette, such as are known in the art. If sample 70 has a statistically valid amount of pollen relative the original tassel(s), a smaller sub sample 90A, would also. Again, knowing the volume of the sub sample relative to either the known volume of the sample (or the original tassel matrix), allows simple calculation of total pollen from the tassel(s) from a quantification of pollen in the sub sample.

FIG. 6 diagrammatically illustrates such a sample and sub sample process. A filtered aliquot is taken with syringe 60 (e.g. 3 mL capacity) from a 3000 mL (3 L) starting tassel matrix 30 and a sample 90 (e.g. 0.8 mL) is placed into mini tube vial 77 (e.g. 1.1 mL capacity mini tube from VWR International, Inc., West Chester, Pa. USA—available in 96-well format rack for use with 96-well plate and automated liquid handling equipment). A 0.04 mL sub sample 90A is collected from mini tube vial 77 and deposited into well position Row A Column 1 (or A1) of tray 88. Thus, sample 70 is approximately 0.10 percent of the original matrix volume. Sub sample 90 in the mini tube 77 is about 0.0267 percent of the starting matrix volume. Sub sample 90A in the well is 0.00133 percent of the starting matrix volume. The sub sample is therefore a quite small fraction of the starting matrix.

Placing sub samples 90A in individual wells 89 of tray 88 is a convenient way to keep correlation of the origin of the sub sample. The identifying information on syringe 60 can be recorded and correlated with the well position (A1, A2, A3, . . . , B1, B2 . . . , etc.) of tray 88. Thus, even though quite small in volume, the sub samples have correlation to the syringe, and the syringe to the specific tassel(s).

As illustrated in FIG. 6, it is sometimes desirable to have replicates of the same tassel matrix 30. For example, first, second, and third sub samples 90A could be taken from the same sample 90 in mini tube vial 77 into three separate wells A1, A2, and A3. Also, sub sample volume can be selected to allow addition of other things into the wells. As indicated diagrammatically in FIG. 6, other substances (e.g. NaOH) could be added into the wells, as has been described.

The use of mini tube vial 77 allows a very precise sample volume to be obtained and deposited from syringe 60, so that, in turn, a very precise volume can be obtained and deposited from mini tube 77 into a well 89. The use of mini vials 77 also allows an intermediate step of storage and organizing samples 70. The first sample 70, taken from the volume extracted by the syringe or otherwise, could be placed in such an intermediate container (e.g. approximately 1 mL capacity mini vial 77) for storage until a sub sample 90A is needed for quantification. A set of mini vials 77 (and mini-vial rack with 96 indexed positions) could be used, each corresponding to a well in a multi-well tray. Then, when a sub sample is taken from a mini vial and placed in a well in the tray, correlation would be maintained. A substance such as NaOH of known amount could be added to the mini vial to help preserve or help the pollen fluoresce if imaged.

2. Imaging and Quantification

The preceding pollen extraction process allows preparation of a representative sample or sub sample of pollen from one or more tassels. The following process generally describes how the pollen in the sample or sub sample can be relatively quickly quantified, and for a relatively large number of samples.

a) Sub-sample Preparation

Using the sample storage and isolation technique of tray 88 has been found to also present the sub samples in good form for imaging, and then utilization of image evaluation software to derive a pollen count from the image.

As many sub samples as can fill tray 88 can be deposited in its wells. Tray 88 is transparent. Therefore an image can be taken either through the open top of a well, or through the transparent bottom of the well. Sometimes a transparent sheet or film is placed over the top of tray 88 to secure the sub samples in place.

Trays like tray 88 are of a size and configuration that is commonly used in laboratory settings to do such things as evaluate the contents of each well under a microscope. However, other containers for samples could be used.

b) Imaging Station

Any of a number of commercially available imaging stations can be used to obtain quite high resolution images of a portion of each well. Station 100 would be used to image each well containing a sub sample of tray 88. Software compatible with station 100 can be programmed to automatically move a stage holding the tray 88 in three orthogonal directions, operate a light source to supply a desired color or wavelength(s) of light during imaging, and take the images.

FIG. 8 illustrates one such station 100. A microscope 102 has optics 106 that allow it to view objects placed on a movable stage 104. As shown, stage 104 is above the optics for microscope 102. As previously mentioned, this was found to be advantageous because the pollen grains in the sub samples 90A in wells 89 of tray 88 tend to fall by gravity to the bottom of wells 89. They thus tend to end up in or close to a single plane relative to a plane that can be focused by the microscope and imaged by the camera 110. Light 108 can produce the appropriate wavelength to cause fluorescence of the pollen in the presence of the NaOH. Other light sources should normally be turned off or substantially attenuated during imaging.

One example of station 100 is an AxioVision system (from Carl Zeiss MicroImaging GmbH, Gottingen, Germany), a fully integrated "turn-key" system, including a Zeiss Axiovert 200 M inverted microscope with a MAC 5000 automated stage digital and camera (e.g. AxioCam), a computer workstation, and AxioVision image evaluation software (see FIG. 8). It allows efficient acquisition of digital images of many samples. The images can be displayed, archived, and evaluated, and can be created in many formats (e.g. bmp, zvi, jpg). In this case, the software identifies objects in the images that meet pre-programmed measurements or characteristics, and counts all such objects. The system makes quantitative measurement of objects in the images and stores the counts with information that correlates the count to sample identification. The software allows interactive measurement tools and parameters (e.g. scaling, length, outline, angle, circle, event counting). The correlated count and sample i.d. information can be placed in a database for further use (e.g. use the count of pollen from the sample to estimate total pollen for the tassel or plant). After calibration, the system can automatically take sequential images of multiple samples (or replicates of samples), archive the images in searchable format, and repeat for a next set of samples. The system can evaluate, measure, count, and store the results. The system can be programmed to perform calculations on the counts to extrapolate information from them. The system includes functions like sample positioning, automatic focusing, image acquisition in several fluoresce channels, acquisition of image series from different focus positions, acquisition of image series over time, automatic measurement (programmable), image cataloging and archiving (searchable), recording and automatic execution steps. Measurement can be based on a wide range of parameters (e.g. geometric and/or densitometric).

Imaging system 100 has interactively motorized microscope and stage control. Operation parameters can be stored so they can be repeated for multiple samples 90 or multiple trays 88, which thus increases speed of image acquisition for many samples. Measurement data is easily exported to most spread sheet programs, including Microsoft Excel. ZVI format allows the image data to be stored in digital memory together with image number, acquisition date, microscope settings, exposure data, size and scale data, contrasting technique used, and other data. Non-complex configuration wizards allow the user to create a desired measurement program. Parameters describing the specimen can be determined by the user interactively. Those parameters can be instructed to be executed in a particular order. Automatic measurement of the high resolution images can be by length, area, perimeter, circle, angle or other geometric or densitometric parameters. The software automatically counts and/or marks events on images based on the programmed measurement parameters.

Additionally, joystick 120 allows quite minute manual, interactive user control of position of stage 104, and thus tray 88 on stage 104, to allow user control of position of each well 89 of tray 88 relative to the field of view of the microscope 102. The user can look through microscope 102 to precisely adjust a well relative to the field of view. The user can also adjust the focus of the microscope relative the well or the bottom of the well. These operations and functions are well known with respect to such imaging stations.

A digital camera 110 is operatively and optically integrated into station 100 and can image essentially at least a portion of what is in the field of view of microscope 102. By these methods, one or more images of each well can be taken. The digital images can be stored in memory or displayed on display 116 of computer 112. These steps allow a digital image of each sub sample, with pollen at or near the focal plane of the image, to be obtained.

It is to be understood that all of the well 89 can be imaged, or a fraction of it. If a fraction, the precise fraction should be recorded or stored, and used in estimating total pollen in the sub sample in well 89. FIG. 7 shows that imaging station 100 is set to image portion 132 of each well 89, which in this example is around 30% (specifically 29%) of the total area of well 89. Portion 132 is chosen to be generally in the center of well 89. FIG. 9 is a picture of an image of a portion of a well 89, and the general appearance of typical objects that would appear in such an image. Note how the objects (mostly pollen grains) appear relatively well distributed across the image plane, however, some are adjacent, abutting, or even overlapping one another. Note too how the background is dark and the objects have varying levels of brightness relative the background. This is caused, in this example, by fluorescence from the pollen grains.

c) Computer and Image Recognition Software

Commercially available image evaluation software (e.g. AxioVision from Carl Zeiss MicroImaging GmbH) can be used with imaging station 100 and computer 112 to produce a count of discernable objects in the image that match criteria consistent with a pollen grain. Such criteria can be programmed via the software. The software can be instructed to automatically produce the count. Some software allows the user to override or change the count. This could occur, for example, if the user displays the image on computer display 116 and sees that the software has either preliminarily counted or failed to count an image object. The user can, by visual examination of the displayed image or by use of microscope 102, determine whether a count should or should not be made, and change the software's count.

Specific functions and aspects of such image evaluation software are well known in the art. One example of such software and how it can be programmed and function in the context of counting pollen has been described previously.

Once a count has been established for a sub sample 90A in a well 89, it can be stored in electronic memory or a database with correlation of the count to the sub sample. As can be appreciated, the automated imaging of each sub sample, and the automated image evaluation counting, can be carried on quite efficiently and quickly from sample to sample. The results are quickly and conveniently stored. The computer can be programmed to automatically calculate an estimation of total pollen per tassel for each sub sample based on the correlated knowledge of the tassel(s) placed in the tassel matrix 30, volume of water added to blender container, and the volume of sub sample 90A taken from matrix 30 (and the area of coverage of the image of well 89 relative to its total area).

In imaging station 100 for corn pollen, the software first (1) picks the parts of the image that are brighter than the background and then (2) picks collections of pixels that match measurement parameters set for a pollen grain (e.g. diameter (for corn pollen 50-120 microns), contrast, brightness, roundness). The software allows the user to view the image on display 116. In one example, the software automatically colors (e.g. green) or otherwise marks image objects it has concluded are pollen grains, but colors (e.g. red) or otherwise marks image objects it determines may be pollen grains. The user can review the display 116 (or look at the actual sample through microscope 112 if the sample is on stage 104) and can decide whether to reject any green object from the count or add any red object (or any other object). The user may even edit the count if it is determined additional pollen grains are present (e.g. if one is directly over another and only one is identified and counted by the software).

As indicated earlier, fluorescence of corn pollen after soaking in NaOH is enhanced in the presence of appropriate wavelength light. The software controls not only the operation of camera 110 and the movement of stage 104, but also the operation of light 108.

The software and imaging station can produce a library of images, magnified through microscope optics. The user enters sample volume and extraction volume. These values, along with the percent area of the well that is imaged and the pollen count from the image, are exported to an Excel spreadsheet. With this information, the Excel program calculates a quantification of pollen. From knowing the pollen count of the imaged portion of the well, it extrapolates how many total pollen were in the blender matrix, and from the number of tassels in the blender matrix, pollen per tassel can be estimated. This information can be automatically saved with correlation to sample name.

3. Count Calculation

Below is an example of how pollen per tassel is calculated in the context of the specific pollen extraction and counting protocols described hereafter:

$$\text{Pollen/Tassel}=[(100/\text{percent of well area imaged}=29)\times(3000\text{ mL water}/0.04\text{ mL placed in well})\times\text{pollen per image}]/5\text{ tassels}$$

The example is based on 3000 mL water and five tassels combined in the blender. About 1 mL sub-sample is obtained. Since the dilution of the 1 mL sub sample is the same as the 3000 mL solution, no calculation is required. From the 1 mL sub-sample, a 0.04 mL sub sample is obtained and placed in a well of known surface area. An image is obtained of the pollen sitting on the bottom of the well. The area of the image is 29% of the bottom surface area of the well. Therefore 29% of the pollen in the well 89 is captured in the image. Pollen in the image are counted.

Thus, quantitation of total pollen per tassel can be derived from the small sub sample 90A by using quantitative methods with original matrix 30, sub sample 90A and image area 132 of well 89.

E. Specific Examples

Following are specific examples of, first, a pollen extraction protocol that can be used with the apparatus and methods described above and illustrated in FIGS. 1-7, and second, a pollen imaging and quantification protocol that can be used with the apparatus and methods of FIGS. 8-10. Citation to reference numbers in the Figures has been added in certain locations.

1. Example of Pollen Extraction Protocol

Pollen Extraction from Tassels Protocol

This protocol is to be used for extracting pollen from tassels and a subsequent counting procedure.

1) If necessary, fill out a chain of custody form for the tassels.

2) Record all sample names and assign them lab numbers using the MS EXCEL template named "Pollencount Tassel Samples Barcode 96 well 3 reps".

3) Put on PPE safety glasses (required), ear plugs (required), neoprene gloves (recommended) and lab coat (optional).

4) Quantitatively transfer a set of five tassels to the special extraction container (28) for use with the blender. If the tassels were collected in water soluble bags (14), add the entire bag (14) to the container (28). Verify that 5 tassels were indeed collected for sampling. Add 3000 mL of water (or 2990 mL of water if tassels are in water soluble bags (14)) to the blending container (28) using a liquid dispensing pump (e.g. Wheaton Science Products, Millville, N.J. (USA) Catalog No. 374301—refer to the owner's manual for calibration instructions). If water soluble bags (14) are used in the extraction process, add 10 mL of antifoam reagent (dimethylpolysiloxane) to control foaming during blending. If any variance in number of tassels extracted or extractant volume is changed, then record the modifications since these numbers are used later in the Microsoft EXCEL template to calculate #pollen/tassel. Note that any number of tassels or tassel parts can be extracted with any reasonable volume of water. A smaller sized blending container such as a 1 L plastic bottle (28B) or a 1 L stainless bottle should generally be used if less liquid volume is used, however, so that an accurate sub sample can be collected through the sideport filter (58). Care must also be taken to use the correct calculations in the MS EXCEL templates if modifications are made.

5) Attach a 3-way valve (67) to the extraction container (28) and a 3 mL disposable syringe (60) to the valve (67). Label the syringe (60) to correspond with the sample number. Make sure the outlet valve (67) is shut so that no water leaks from the blender (20) during blending.

6) Position the container (28) onto the blender base (22) and start the blender (20) on low speed. After the unit comes to speed ~10 seconds, switch to high speed and blend for 4 minutes. If any unusual noise (grinding) or heavy leakage occurs, stop the blender (20) and adjust the container (28).

7) At 4 minutes, equilibrate the syringe (60) with the extract by filling and ejecting the syringe ~3 times back and forth quickly. Finally, pull a 3 mL sample (70) using the syringe (60), close the valve (67), and place a ~0.8 mL sub sample (90) into a prelabeled VWR minitube vial. Perform this operation three times/sample to ensure three replicates have been collected in three different mini tube vials.

8) If samples (90) cannot be processed in the same day, then the samples must be stored in the refrigerator to reduce microbial growth. If samples need to be stored longer than a week, add 5 μL of 10M NaOH as preservative and store in the refrigerator.

9) When the samples (90) are ready for analysis, place the vial rack onto the liquid handling system (86) for sub sampling into one or more 96 well plates (88).

10) Prepare the sample for use in the Pollen Counting Protocol (set forth below). A 40 μL representative sub sample of pollen suspension should be transferred from the minitubes to the 96 well plate (88). Also 160 μL of 1M NaOH is added to each well. Note that any volume combination that does not exceed the well volume can be used to optimize pollen counting. However, the amount of sample transferred into the wells must be known for inputting into the MS EXCEL spreadsheet calculations.

11) Place a film seal on the plate (88).

12) Put the plate (88) on the shaker (e.g. Lab Line model titer plate shaker from Cole-Parmer Instrument Company, Vernon Hills, Ill. USA) @1000 rpm for about 30 seconds to distribute pollen evenly in the wells.

13) If possible, let the plates (88) sit for >4 hours to enable the NaOH to act on the sample by reducing background fluorescence and evening out pollen fluorescence. Reshake the pollen after soaking to ensure even pollen distribution in the wells.

14) After any shaking operation, let the pollen settle for at least 10 minutes or until floating pollen have sunk to the bottom. Floating pollen may not be counted during the image analysis and may reduce the quality of the image due to fluorescence scattering (ghosting or bright background spots) in the image.

15) Perform image analysis according to Pollen Counting Protocol or another counting method.

16) Dispose of pollen samples into approved waste containers for sodium hydroxide.

2. Example of Pollen Quantification Protocol

Pollen Counting Protocol

This protocol is to be used for the quantitative determination of pollen in liquid media arising from tassel extraction using an imaging station including a Zeiss Axiovert Microscope, Zeiss Axiovision image recognition software, and Microsoft EXCEL software for storing pollen counts correlated to identifying information about the source of the pollen.

The following assumptions are made when using this protocol.

a) Pollen samples have been prepared according to appropriate sample preparation protocols.

b) This protocol is for counting pollen only. Pollen sizing, fluorescence properties, viability estimation, and other characteristics can be determined using different protocols and/or automeasure settings.

c) Compatibility with Zeiss Axiovision versions v4.4 and v4.5.

d) Maize pollen are 50 to 120 microns in diameter, mostly spherical, and are blue-green autofluorescent.

e) For tassel extracted pollen, three method replications are placed in three consecutive wells of a ninety-six well microplate (88) ordered from left to right and then top to bottom; beginning with sample 1 in position A1 of the microplate.

f) Image archive naming protocol and subsequent data table.CSV file naming protocol is followed exactly.

g) Ninety-six well surface area=28,748,820 um$^2$.

Procedure

1) Switch on the microscopy computer (112) and log on to the network (e.g. intranet).

2) Switch on the microscope (102), stage (104), and fluorescence lamp (108).

3) Open Zeiss Axiovision v4.4 software on computer (112). Verify that the toolbars, settings, and scalings are installed and the screen (116) appears as shown in FIG. 10.1.

4) Begin a pollen analysis experiment by clicking the FITC setting button on the toolbar. Turn off any overhead lights and at least partially close the door to the darkroom to prevent stray light from interfering with the image analysis.

5) Place 96 multiwell plate (88) on the stage (104) with well #A1 positioned at the top left hand side of the stage (104) and use the joystick (120) to move the stage (104) to the approximate center of well #A1 (or a well that contains a pollen sample (90, 92, or 94) that needs measured.

6) Click the live (camera) button on the toolbar and then click the MRM button on the toolbar (FIG. 10.2). Click the measure button in the MRM window to set the camera exposure time (should be 6-9 s) and then manually focus the image to ensure that the pollen are in focus. Right click on the window to verify the "fast" acquisition mode is selected (checked). Note that the mode can be changed, but needs to be on "fast" for the autofocus module to work properly as calibrated for the pollen experiment.

7) The MRM and live windows can now be closed.

8) Click the Mark and Find button (FIG. 10.3) on the Axiovision toolbar to set up the stage (104) positions for each sample (well).

9) Select the appropriate multiwell format from the options list. e.g. 96 multiwell format (FIG. 10.3). Preferably, use the "96 well" option because these have been preprogrammed specifically for the pollen experiments. If the default 96 well formats are selected, then the well numbering system needs to be verified visually during the experiment to ensure image naming corresponds to the right sample well.

10) Clear all marked positions by clicking the trash can icon on the multiwell graphics tab (FIG. 10.3).

11) Start the well plate (104) position calibration wizard by clicking the wizard icon in the right hand corner of the multiwell graphics tab (FIG. 10.3).

12) Follow the instructions of the calibration wizard to mark all the sample wells for imaging (FIG. 10.4). Choose "No" for using the current calibration data. If the window does not contain a crosshair or does not move correctly, then close the Mark and Find wizard and restart the wizard. Be sure the pollen are in focus during the Mark and Find process. However, if needed, the Z (focus) depth can be changed on the "positions" tab.

13) When the wizard completes, highlight the wells that you want to image on the multiwell graphics tab and push the C button to generate center positions for the wells (FIG. 10.5).

14) Click the positions tab (FIG. 10.5). Center positions for each well should appear. Double click the first position (A1) and verify that the stage moves to well #A1. Click the Live button to view the pollen sample in the well. If the pollen are not sharply in focus, then manually focus the microscope until the pollen are sharp. Then close the live window and click the z icon on the positions tab to change the z setting. All z positions should change to the same value. The z value corresponding to the correct focal distance for the pollen imaging is usually an important step since the autofocus cannot correct for extreme out of focus events. Out of focus image acquisition should be avoided.

15) Push the Save button and then close the Mark and Find window.

16) Open the multidimension acquisition window by pushing the 6-D acquisition button on the toolbar (FIG. 10.6). On the Experiment tab, choose load "96 well" for a 96 well tassel pollen analysis experiment.

17) Click on the Mark and Find tab of the Multidimensional Acquisition window and push the "get list" button. At this point the positions that you made in the Mark and Find (step 14) should transfer to the multidimensional experiment. Check the "use Z" button is on (FIG. 10.7).

18) Click back on the Experiment tab of the Multidimension Experiment window.

19) Save the experiment and turn off the overhead lights (if not already off).

20) Push the start button to begin the image acquisition of the wells (the stage should move automatically).

21) During the image acquisition the screen should appear as in FIG. 10.8.

22) It is a good idea to watch the first couple of images being acquired to ensure that the stage is moving properly, the pollen are in focus, and that image A1 is actually from well number A1.

23) When images of all the wells have been acquired, you may either load another multiwell plate for analysis or close the archive of images to begin the pollen counting process. If you wish to analyze another plate, then remove the old plate and insert another plate of the same kind (be sure Al is top left on the stage) and push the start button. The "positions" list will should not have to be altered unless the microscope (102), stage (104), or computer (112) is turned off. The positions list generally has to be reset each day. Note that the naming protocol for each multiwell plate experiment has been set to the following archive format: Year, Month, Day, Counter value (FIG. 10.9). Each image within the plate (104) is also assigned the well number from which the image was acquired. Thus each sample that is analyzed is automatically assigned a unique identifier code that is used during the pollen counting process. The archive is saved automatically and requires no user input. The archive name should not be changed from default setting if the Microsoft EXCEL template is used for pollen counting.

24) To analyze an image archive from each experiment (multiwell plate), click the "run automeasure prog." button on the toolbar.

25) Choose the pollen2.5x program (FIG. 10.10).

26) Choose the "folder" button for analyzing an archived experiment.

27) Navigate the path to the image archive to be analyzed.

28) Choose the .ZVI format and make sure the Automatic button is checked (on).

29) Uncheck the "append data to file", check the autosave, and apply scaling from image buttons. Make sure the scaling file is 2.5x vert. and the AutoSave button is checked (on).

30) Push the execute button.

31) You will first have to separate pollen from the background and debris based on contrast of fluorescence intensity (FIG. 10.11). This is done by clicking on any pollen that are not highlighted in red (based on preprogrammed contrast definitions). If large portions of the image background turns red, the contrast may need to be reset. Push the reset button on the left and then click on the pollen to highlight.

32) Once all of the pollen are highlighted with minimum or preferably no background highlight, click Continue. Then all the pollen that were found automatically will either be outlined in green on the computer display (116) by the Axiovision software (counted) or red (not counted) (FIG. 10.12). Click once on a pollen to either count or not count a pollen that was missed or over counted (e.g. debris). Click Continue to automatically analyze the next sample in the archive for analysis. Not more than 400 pollen should appear in the image for accurate counting. If more than 400 pollen were found, then a note should be made for that sample and the sample should be reanalyzed at a lower concentration. Also, if anything goes awry with the image analysis, e.g. not enough pollen was counted or there are big pollen clumps, then a note should be made regarding that sample and the sample reanalyzed.

33) The data will automatically move into a table called (Pollen2.5x_flds). There should be an image name, the pollen count, and the area (be sure the area unit is $\mu m^2$) in the table. This table is in .CSV format and will be directly imported into a Microsoft EXCEL pollen counting template.

34) When all the images from an experiment have been analyzed, you must save the flds file by adding the archive code to the name (FIG. 10.13). This naming protocol will be used in the Microsoft EXCEL pollen counting template.

35) The following steps can be done on any computer with Microsoft EXCEL and network access to the EXCEL pollen counting template and pollen.csv files you created in step 34. To import the .CSV data into EXCEL, open the pollencount template or EXCEL file (if sample names have been entered) that is appropriate for your experiment, e.g. 96 well tassel pollen. Upon opening, select "yes" to enable macros and "no" to autorefresh (if autorefresh flashes).

36) Assuming that all sample names have already been entered, click on the Count P1 sheet. And then place the cursor in an empty cell on the left hand side of the sheet. From the toolbars menu, select Data, Refresh Data, and then navigate to the .CSV file that corresponds to the pollen count results for plate 1 of your sample analysis (FIG. 10.14). Note that you may need to select the all files button and refresh the data if the .CSV file that you are looking for does not show up immediately. If that does not work, shorten the default name to help find the file you are looking for.

37) Once the data has been imported, it needs to be put into the proper numerical order, given the correct well assignment and sorted. This is done with an EXCEL macro called ReplaceCount (FIG. 10.15).

38) On the tools menu, select "macro" or "macros" and then highlight the Replace Count macro and hit Run. The data should be reassigned a name, the column headings should change, and the data should sort automatically.

39) Enter the appropriate sample volume and extraction volume in the designated cells to make the correct calculations for the sample analysis (FIG. 10.16).

40) Repeat steps 36-38 to import data for additional plates which have been analyzed.

41) A summary sheet provides compilation of all data from each individual plate analysis and with sample names so that the user ultimately has a sample name with a corresponding pollen count and some statistics regarding the analytical confidence. Typically, the CV % (coefficient of variation %) should be <20% for the analysis. At very low pollen concentrations this parameter may not hold. The end user is responsible for setting the analytical criteria for acceptability (FIG. 10.17).

42) When the analysis is finished, dispose of the pollen samples properly into waste containers.

F. Applications

The ability to quantify pollen, with sufficient accuracy, speed, reliability, and repeatability over a range of sizes, allows a substantial number of applications. Examples will be discussed below.

1. Prediction of Genotype

Accurate quantification of per plant pollen allows for statistically valid comparison of pollen production between different plants or varieties of plants. In turn, this can lead to other evaluations.

For example, variation in pollen production by inbred genotype and environmental effect on pollen production can be evaluated. Tables 1 and 2, below, provide results of such studies. As can be seen, variations based on these types of distinctions are demonstrated. Such results can assist plant scientists and breeders to make selections of plants that exhibit desirable traits or characteristics for a given goal. The goal can be further breeding or genetic advancement, commercial production of the selected variety or genotype, or others, such as are known by those skilled in the art.

Tables 1 and 2 demonstrate correlations that can be advantageously used with quantitative pollen counting. Small plot trials were established at eight research sites. These sites include Aussonne France, York N.E., LeRoy Ill., Constantine Mich., Tipton Ind., and Algona, Dysart, and Johnston Iowa. The experiment included twenty-four inbred maize genotypes with two replications at each location. Five tassels were collected from each experimental unit just prior to pollen shed. The tassels were dried and pollen extracted. The number of pollen grains per tassel was determined. Results from this experiment are provided to demonstrate that the environment does influence the number of pollen grains produced per tassel (Table 1) and that there is genetic variation in number of pollen grains produced per tassel among the 24 inbred maize genotypes studied (Table 2).

TABLE 1

Number of pollen grains per tassel across 24 inbred maize genotypes at each of the 8 testing locations. These data show the environmental effect on the number of pollen grains produced per tassel.

| Location | Average number of pollen grains per tassel | tGrouping* | Number of data points | Standard Deviation |
|---|---|---|---|---|
| Europe Parent Test (France) | 13,900,000 | A | 42 | 5,700,000 |
| York NE | 12,900,000 | B | 44 | 4,400,000 |
| LeRoy IL | 12,300,000 | CB | 45 | 4,300,000 |
| Algona IA | 12,000,000 | C | 47 | 4,300,000 |
| Constantine MI | 10,600,000 | D | 47 | 3,900,000 |
| Dysart IA | 10,000,000 | D | 48 | 3,900,000 |
| Johnston IA | 8,500,000 | E | 48 | 3,700,000 |
| Tipton IN | 7,600,000 | E | 48 | 3,400,000 |

*Locations followed by the same letter are not significantly different at the 0.05 probability level

TABLE 2

Average number of pollen grains per tassel by inbred maize genotype across 8 testing locations. This table demonstrates the variation in number of pollen grains per tassel among the 24 maize inbred genotypes tested. Some inbreds produce 3 times more pollen grains than other inbreds.

| Maize inbred genotype | Average number of pollen grains per tassel | tGrouping* | Number of data points | Standard Deviation |
|---|---|---|---|---|
| A | 16,300,000 | A | 15 | 5,700,000 |
| B | 15,900,000 | AB | 16 | 4,800,000 |
| C | 15,900,000 | AB | 16 | 4,900,000 |
| D | 15,600,000 | AB | 16 | 4,000,000 |
| E | 15,400,000 | AB | 15 | 3,000,000 |
| F | 14,600,000 | BC | 16 | 3,400,000 |
| G | 13,200,000 | CD | 15 | 3,100,000 |
| H | 13,000,000 | D | 15 | 3,200,000 |
| I | 11,900,000 | DE | 16 | 3,500,000 |
| J | 11,200,000 | EF | 16 | 2,600,000 |
| K | 10,600,000 | EFG | 16 | 3,500,000 |
| L | 10,100,000 | FGH | 13 | 3,500,000 |
| M | 9,700,000 | FGH | 16 | 3,900,000 |
| N | 9,400,000 | GHI | 16 | 2,700,000 |
| O | 9,200,000 | GHI | 14 | 2,900,000 |
| P | 8,800,000 | HIJ | 15 | 4,600,000 |
| Q | 8,200,000 | IJK | 16 | 2,300,000 |
| R | 8,200,000 | IJK | 16 | 1,800,000 |
| S | 8,100,000 | IJK | 16 | 2,200,000 |
| T | 8,000,000 | IJK | 16 | 2,700,000 |
| U | 7,900,000 | IJK | 14 | 2,100,000 |
| V | 7,500,000 | JK | 15 | 3,200,000 |
| W | 6,900,000 | K | 14 | 1,500,000 |
| X | 4,900,000 | L | 16 | 1,400,000 |

*Inbreds followed by the same letter are not significantly different at the 0.05 probability level 2. Ability of Inbreds to Produce Pollen As discussed earlier, accurate pollen count can be used to determine the ability of an inbred to produce sufficient pollen to be successful as a male in commercial seed production. Knowledge of the amount of pollen production can be also advantageously applied in the production of male-sterile hybrid seed. For example, the cost of production of male-sterile hybrid seed is typically less because of reduced costs of not detasseling the female during seed production. Having the proper blend ratio of male-sterile and male-fertile hybrid seed ensures adequate pollen for hybrid grain production while keeping seed production costs to a minimum. Knowledge of likely pollen production in advance can help achieve the proper blend.

3. Tassel Traits

Pollen count can be used to identify tassel traits that best correlate with pollen production, determine genetic variation in pollen production, and identify markers associated with tassel traits that best correlate with pollen production.

4. Genetic Gain

Another example involves surveying species, crops or weeds, for ranges in pollen production. Such could indicate ability to produce genetic variability beneficial for adaptation and ability to disperse genetic material.

5. Fecundity

Another example is use of the method or apparatus to estimate or predict the ability to reproduce (fecundity).

G. Options and Alternatives

The above detailed description is for illustrative purposes only and is not comprehensive of the different forms, aspects, or embodiments the invention can take. Variations obvious to those skilled in the art are included within the invention. Some examples follow.

The extraction aspects can be practiced with or without the quantification aspects. For example, pollen can be quantified in different ways, including hand counting or use of other devices or methods (intensity readings while moving past a sensor; laser sizing, etc.)

Likewise, the quantification aspects can be practiced with or without the extraction aspects. For example, pollen can be collected in other ways, including both pre- and post-shed. Also, pollen of other types of plants, or even non-pollen particles, could be quantified using the described principles.

Examples of other plants include, but are not limited to, rice, maize, soybean, wheat, canola, sunflower, alfalfa, sorghum, pigweed, sugarcane, and other flowering plants. Examples of non-pollen particles include, but are not limited to, soybean cyst nematode, disease spores, seed of small seed plants such as tobacco, and European corn borer egg number.

These non-limiting examples illustrate how the described methods and apparatus can be applied in a variety of ways to pollen from other than maize and to non-pollen particles.

The use of a bag 14 is optional. Other containers or carriers could be used.

Different configurations and sizes of container 28 could be used.

1. Pestle and Mortar Separation/Mesh Screen Extraction

An alternative way to extract corn pollen from anthers uses a pestle and mortar in isotonic solution. Additionally dry grinding could also be performed. A 53 and 120 micron mesh screen separates the pollen grains from other plant tissue. An alternative way to quantify pollen uses a Coulter principle method to size and count particles, such as the previously discussed Coulter Multisizer manufactured by Beckman Coulter, Inc.

2. Staining

By using appropriate stains in the sub sample 90, it may be possible to not only count pollen, but discriminate between counted pollen grains. For example, darker stains can be used to produce an image that distinguishes starch in the pollen grains. It may be possible to determine which pollen were capable of fertilization and which were not. This information could be useful in identifying varieties that have a higher propensity of better pollen viability.

3. Liquid Handling

As mentioned, the addition of NaOH to the wells 89 and extraction of a sub sample from the sample or matrix aliquot could be automated. A wide variety of commercially available equipment could be used. This may speed the process.

Also, as mentioned, sampling from the blender may not need a syringe. An automated liquid handling machine could directly extract it and move it to tray 88.

4. Specific Pollen Grain by Grain Sizing

Pollen enlarges as it develops until it sheds. With appropriate resolution of image analysis software and microscopy, not only can pollen in the digital image be counted based on geometric parameters, each pollen object could be characterized by a size measurement (e.g. diameter). It has been reported that pollen size can have a correlation to pollen viability. Thus, the system could be programmed to estimate the viability of pollen from a plant or a genotype of a plant. Such information could be used to compare pollen viability between plants or varieties of plants for selection or research purposes.

Furthermore, pieces could be cut from different vertical levels of tassels and pollen extracted and size of pollen measured. It has been reported that there may be a correlation between size of pollen from different parts of the tassel and whether the plant might be a short or long shedder. This could be used to determine which plants or varieties of plants are likely the better pollinators. This information could be used for plant selection or research purposes.

The invention claimed is:

1. A method for high throughput quantification of pre-shed pollen of a plant comprising:
   a. providing a plant having a portion including pre-shed pollen;
   b. placing the portion of the plant in a liquid;
   c. blending, in a blender having a rotatable blender blade, the liquid and portion of the plant to create a relatively homogenous liquid suspension;
   d. extracting a sample of the liquid suspension through a filter while the blender is running, the filter having the characteristic of passing the pollen;
   e. placing the sample in a container;
   f. distributing the pollen substantially uniformly in the sample;
   g. acquiring a magnified digital image of a known portion of the sample,
   h. counting objects in the magnified digital image which appear to be pollen.

2. The method of claim 1 wherein the liquid is water.

3. The method of claim 1 wherein the blending with the rotatable blender blade is for a time and at a blade RPM designed to create forces sufficient to destroy the portion of the plant and release the pollen into the liquid.

4. The method of claim 1 wherein the plant is maize.

5. The method of claim 4 wherein the portion of the plant is a tassel or a part of a tassel.

6. The method of claim 4 wherein the portion of the plant comprises a plurality of tassels.

7. The method of claim 4 wherein the blending is in a volume of water of at least one liter, the RPM is over 16000 RPM, and the time of blending is over two minutes.

8. The method of claim 1 further comprising placing the portion of the plant including pre-shed pollen into bag which is soluble in the liquid prior to step b. of claim 1.

9. The method of claim 8 further comprising drying the portion of the plant including the pre-shed pollen prior to step b of claim 1.

10. The method of claim 1 further comprising repeating the steps of claim 1 for one or more other plants.

11. The method of claim 1 further comprising adding a substance to the liquid and particles that promotes higher contrast of particles in the magnified image from background or non-pollen solids.

12. The method of claim 11 wherein the particles are maize pollen and the substance comprises NaOH, and further comprising illuminating the particles with light of a wavelength that promotes fluorescing of the pollen and quenches fluorescing of non-pollen solids.

* * * * *